US012594432B2

(12) United States Patent
Mao et al.

(10) Patent No.: US 12,594,432 B2
(45) Date of Patent: Apr. 7, 2026

(54) THERAPEUTIC APPARATUS AND CONTROL METHOD THEREOF

(71) Applicant: REBECCATECH LLC, Irvine, CA (US)

(72) Inventors: Rongwei Mao, Irvine, CA (US); Yang Zhang, Irvine, CA (US)

(73) Assignee: REBECCATECH LLC, Irvine, CA (US)

( * ) Notice: Subject to any disclaimer, the term of this patent is extended or adjusted under 35 U.S.C. 154(b) by 1253 days.

(21) Appl. No.: 17/465,837

(22) Filed: Sep. 2, 2021

(65) Prior Publication Data

US 2022/0080216 A1     Mar. 17, 2022

Related U.S. Application Data

(60) Provisional application No. 63/079,486, filed on Sep. 17, 2020.

(51) Int. Cl.
  *A61N 1/40*        (2006.01)
  *A61N 1/04*        (2006.01)

(52) U.S. Cl.
  CPC ............. *A61N 1/40* (2013.01); *A61N 1/0472* (2013.01)

(58) Field of Classification Search
  CPC ................................. A61N 1/0476; A61N 1/40
  See application file for complete search history.

(56) References Cited

U.S. PATENT DOCUMENTS

| | | | |
|---|---|---|---|
| 2008/0183251 A1* | 7/2008 | Azar ...................... | A61B 18/14 |
| | | | 607/101 |
| 2009/0036885 A1* | 2/2009 | Gregg ................ | A61B 18/1233 |
| | | | 606/35 |
| 2019/0351224 A1* | 11/2019 | Sano ........................ | A61N 1/40 |

* cited by examiner

*Primary Examiner* — Kaitlyn E Smith

(57) ABSTRACT

A therapeutic apparatus is disclosed, comprising a signal generator configured for generating a therapeutic signal, a treatment head, multiple sets of electrodes arranged on the treatment head, a switch circuit connected between the signal generator and multiple sets of electrodes, and a control unit connected with the switch circuit, and by the control unit controlling on-off of the switch circuit, the signal generator is controlled to be connected with at least one set of electrodes to output the therapeutic signal. Through the therapeutic apparatus, energy can be controlled to be output only to the local area, so as it can be attached to the surface of the skin in the narrow space and treat the skin in the narrow space. When only part of the electrodes are connected with the signal generator, the output power of the signal generator can be concentrated on outputting the therapeutic signal.

16 Claims, 15 Drawing Sheets if a first control instruction is detected, dividing all the electrodes 24 of the therapeutic apparatus into multiple sets of electrodes according to a grouping mode indicated by the first control instruction          S001 choosing at least one set of electrodes from the multiple sets of electrodes          S100 controlling the switch circuit 22 connected between the at least one set of electrodes and the signal generator 21 to be turned on to connect the at least one set of electrodes and the signal generator 21          S200

Figure 25 the switch circuits 22 between all the electrodes 24 and the signal generator 21 are controlled to be turned on, making all the electrodes 24 in the probe 23 connected with the signal generator 21 to output the therapeutic signal          S01 detecting sensing signals by the detecting sensor and determining an usage of all electrodes 24 in the treatment head 23 according to the detected sensing signals          S02 according to the usage of all electrodes 24 in the treatment head 23, determining the grouping mode of all electrodes 24 in the treatment head 23          S03

Figure 26 detecting a first temperature signal through the temperature sensor 252          S112 according to the first temperature signal, choosing at least one set of electrodes from the multiple sets of electrodes          S114

Figure 27

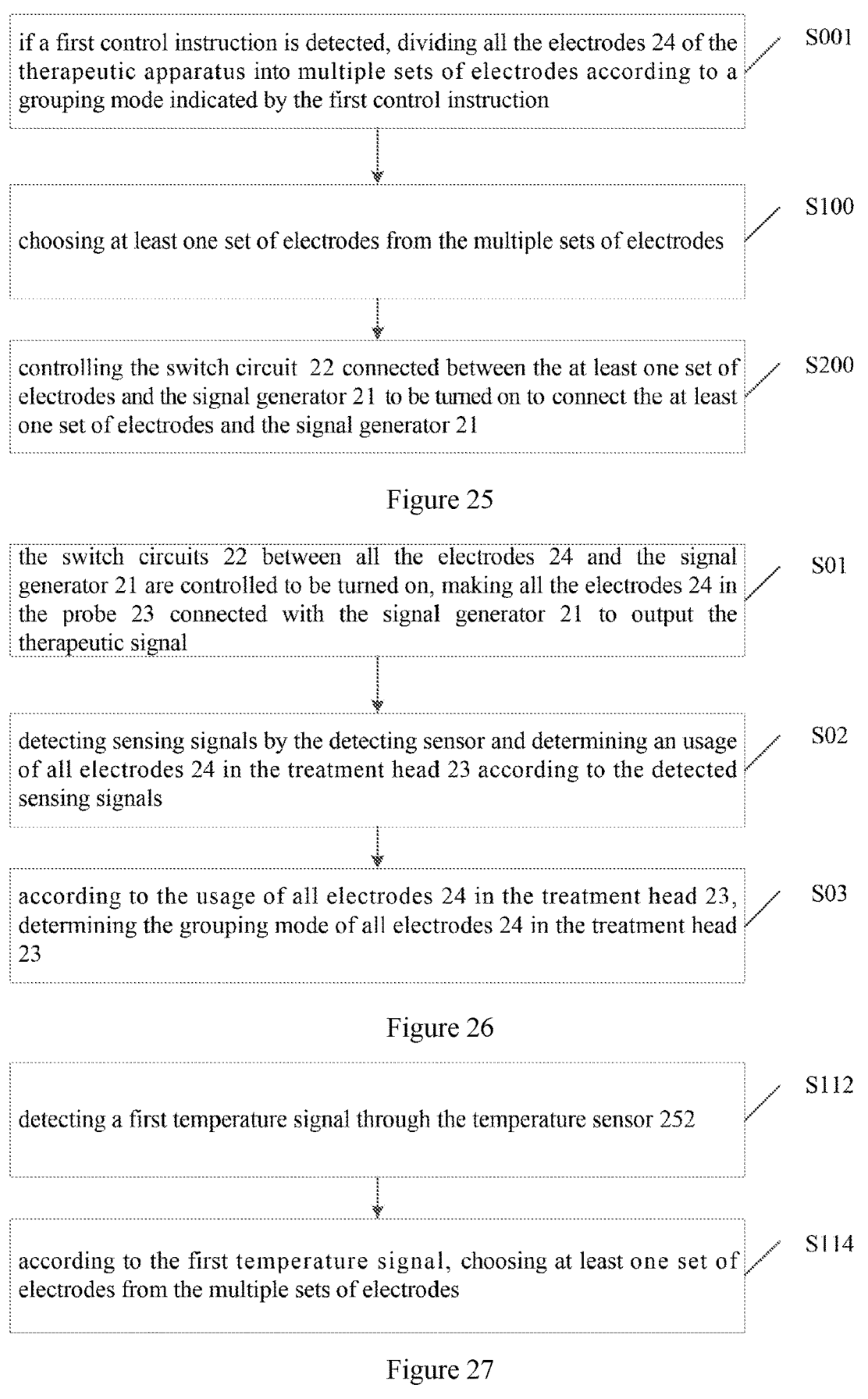

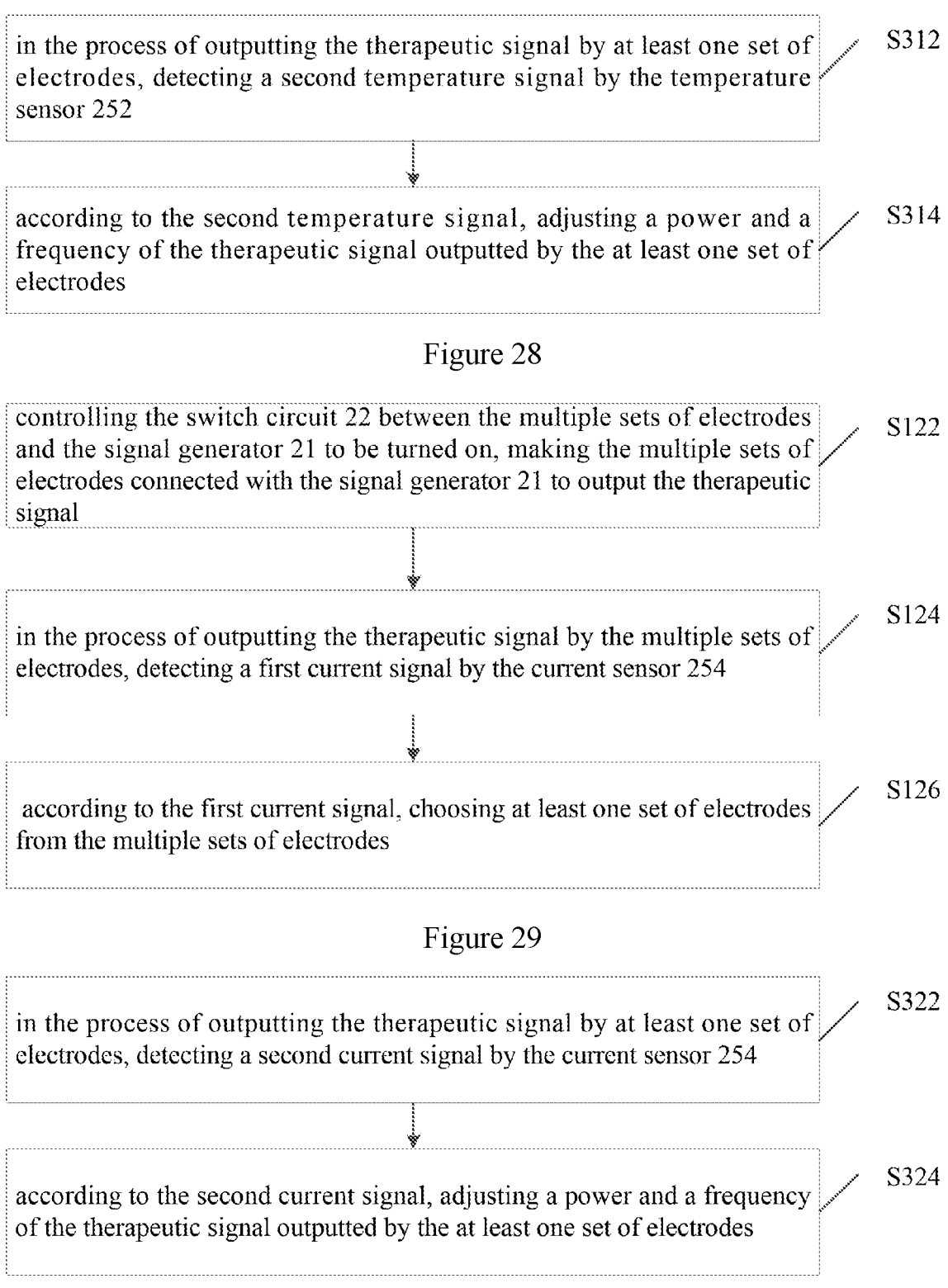

in the process of outputting the therapeutic signal by at least one set of electrodes, detecting a second temperature signal by the temperature sensor 252     S312 according to the second temperature signal, adjusting a power and a frequency of the therapeutic signal outputted by the at least one set of electrodes     S314

Figure 28 controlling the switch circuit 22 between the multiple sets of electrodes and the signal generator 21 to be turned on, making the multiple sets of electrodes connected with the signal generator 21 to output the therapeutic signal     S122 in the process of outputting the therapeutic signal by the multiple sets of electrodes, detecting a first current signal by the current sensor 254     S124 according to the first current signal, choosing at least one set of electrodes from the multiple sets of electrodes     S126

Figure 29 in the process of outputting the therapeutic signal by at least one set of electrodes, detecting a second current signal by the current sensor 254     S322 according to the second current signal, adjusting a power and a frequency of the therapeutic signal outputted by the at least one set of electrodes     S324

Figure 30

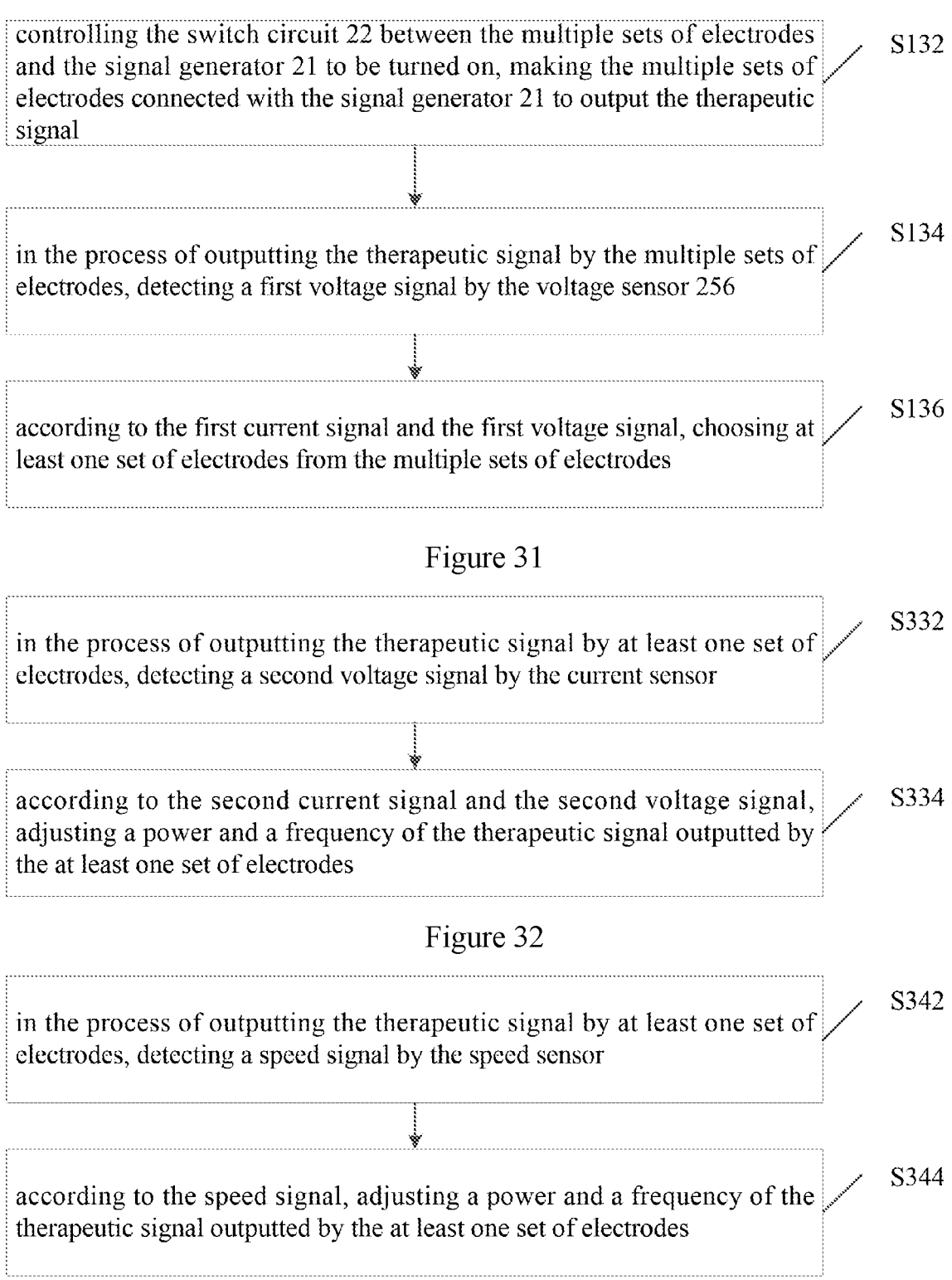

controlling the switch circuit 22 between the multiple sets of electrodes and the signal generator 21 to be turned on, making the multiple sets of electrodes connected with the signal generator 21 to output the therapeutic signal    S132 in the process of outputting the therapeutic signal by the multiple sets of electrodes, detecting a first voltage signal by the voltage sensor 256    S134 according to the first current signal and the first voltage signal, choosing at least one set of electrodes from the multiple sets of electrodes    S136

Figure 31 in the process of outputting the therapeutic signal by at least one set of electrodes, detecting a second voltage signal by the current sensor    S332 according to the second current signal and the second voltage signal, adjusting a power and a frequency of the therapeutic signal outputted by the at least one set of electrodes    S334

Figure 32 in the process of outputting the therapeutic signal by at least one set of electrodes, detecting a speed signal by the speed sensor    S342 according to the speed signal, adjusting a power and a frequency of the therapeutic signal outputted by the at least one set of electrodes    S344

Figure 33 controlling the circuit modulator 220 to make the at least one set of electrodes connected with the signal generator 21 by the circuit modulator 220 to output the therapeutic signal    S210 controlling the circuit modulator 220 to adjust the electric field intensity formed by the at least one set of electrodes    S220

THERAPEUTIC APPARATUS AND CONTROL METHOD THEREOF

CROSS REFERENCE TO RELATED APPLICATIONS

The present application claims the benefit of U.S. Provisional Patent Application No. 63/079,486 filed on Sep. 17, 2020, the contents of which are incorporated herein by reference in their entirety.

FIELD OF THE INVENTION

The present application relates to the field of electronic devices, in particular to a therapeutic apparatus and a control method thereof.

BACKGROUND OF THE INVENTION

Radio frequency treatment has many cutting-edge applications in medicine. The therapeutic apparatus used in radio frequency treatment usually has a treatment head with multiple electrodes. After the electrodes are attached to the skin surface, radio frequency current can be applied to the skin through the electrodes for treatment.

In the related technology, all electrodes of the treatment head must be attached to the skin surface during the treatment process of the therapeutic apparatus, which is difficult to comply to the treatment on an uneven skin surface such as chin or nose.

SUMMARY OF THE INVENTION

A therapeutic apparatus and a control method thereof is provided in the present application, in which the skin in narrow space can be treated by controlling only part of the electrodes on the treatment head of the therapeutic apparatus to output therapeutic signals. The technical scheme is as follows:

Firstly, a therapeutic apparatus is provided, which comprises a signal generator configured for generating a therapeutic signal, a treatment head, multiple sets of electrodes arranged on the treatment head, a switch circuit connected between the signal generator and multiple sets of electrodes, and a control unit connected with the switch circuit. By the control unit controlling on-off of the switch circuit, the signal generator is controlled to be connected with at least one set of electrodes among the multiple sets of electrodes to output the therapeutic signal.

In the present application, multiple sets of electrodes are set on the treatment head of the therapeutic apparatus. The multiple sets of electrodes are connected with the signal generator through the switching circuit, and the on-off of the switch circuit is controlled by the control unit. When the therapeutic apparatus is working, by controlling the switch circuit through the control unit, one set of electrodes or several sets of electrodes among the multiple sets of electrodes are connected with the signal generator to output the therapeutic signal. Through the therapeutic apparatus of the application, energy can be controlled to be outputted only to the local area, which is convenient to be attached to the skin surface in the narrow space to treat the skin in the narrow space. At the same time, the therapeutic apparatus optimizes the output energy of each local area according to the collected sensor signal. At the same time, when only part of the electrodes are connected with the signal generator, the output power of the signal generator can be concentrated on the part of the electrodes that need to output the therapeutic signal, so as to improve the treatment efficiency of the therapeutic apparatus and avoid energy waste. By grouping, the load balance and the RF power output can be optimized. Through the collected sensor data, the energy output to each electrode is optimized to improve the user experience.

Secondly, a control method for controlling a control unit of a therapeutic apparatus is provided, and the therapeutic apparatus further comprises a signal generator configured for generating a therapeutic signal, a treatment head, multiple sets of electrodes arranged on the treatment head, a switch circuit connected between the signal generator and multiple sets of electrodes, wherein, the control method comprises:

step S1, choosing at least one set of electrodes from the multiple sets of electrodes;

step S2, controlling the switch circuit connected between the at least one set of electrodes and the signal generator to be turned on to connect the at least one set of electrodes and the signal generator to output a therapeutic signal.

Thirdly, a computer-readable storage medium is provided. The computer-readable storage medium stores a computer program. When the computer program is executed by a processor, the method described in the second aspect is realized.

Fourthly, a computer program product including instructions is provided to cause the computer to perform the steps of the method in the second aspect when it is run on the computer.

It is understandable that the beneficial effects of the above-mentioned second, third and fourth aspects can be seen from the relevant description in the above-mentioned first aspect, which will not be repeated here.

BRIEF DESCRIPTION OF THE DRAWINGS

In order to more clearly explain the technical scheme in the embodiment of the application, the attached drawings needed to be used in the description of the embodiment will be briefly introduced. Obviously, the drawings described below are only some embodiments of the application. For ordinary technicians in the art, without paying creative labor, other drawings may also be obtained from these drawings.

FIG. 25 is a flow chart of the second control method provided by the embodiment of the present application;

FIG. 26 is a flow chart of an electrode grouping mode provided by the embodiment of the present application;

FIG. 27 is a flow chart of a first selection progress of the electrode provided by the embodiment of the present application;

FIG. 28 is a flow chart of a first output adjustment process provided by the embodiment of the present application;

FIG. 29 is a flow chart of a second selection progress of the electrode provided by the embodiment of the present application;

FIG. 30 is a flow chart of a second output adjustment process provided by the embodiment of the present application;

FIG. 31 is a flow chart of a third selection progress of the electrode provided by the embodiment of the present application;

FIG. 32 is a flow chart of a third output adjustment process provided by the embodiment of the present application;

FIG. 33 is a flow chart of a fourth output adjustment process provided by the embodiment of the present application;

Figure 1:
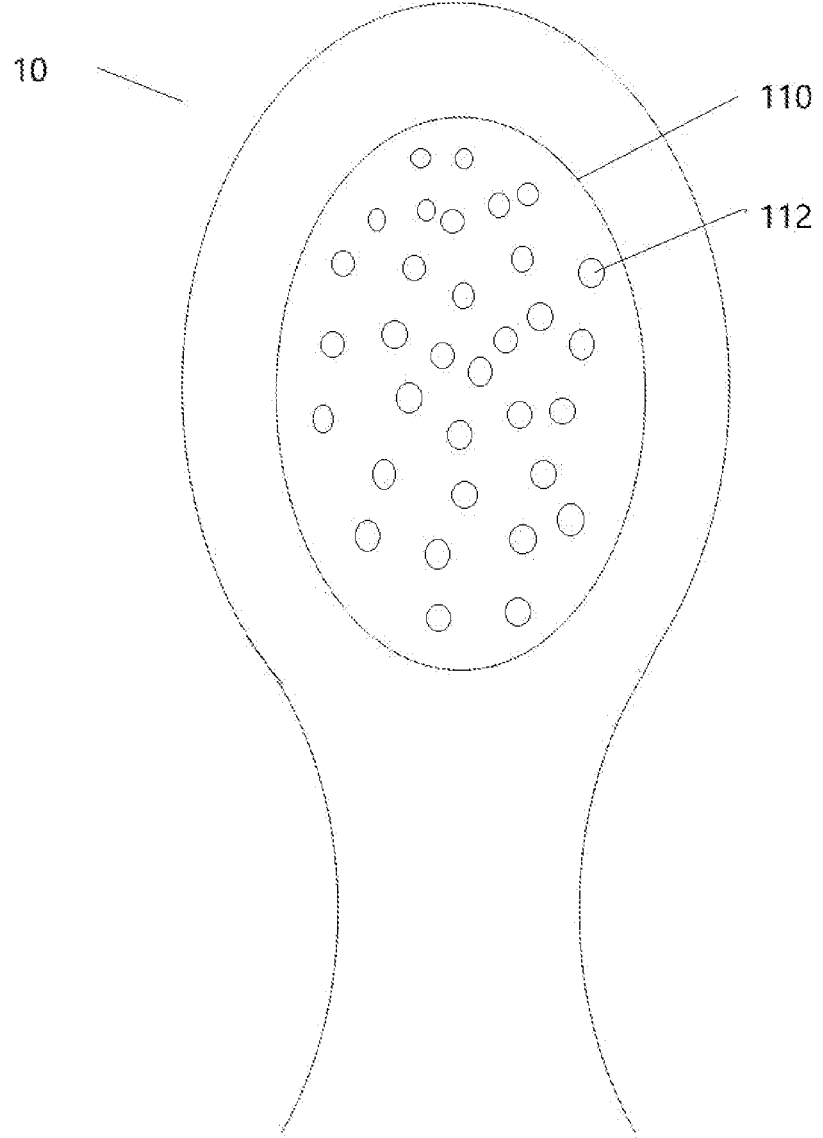
FIG. 1 is a schematic diagram of the appearance of the therapeutic apparatus in the related technology.

Wherein, the meanings represented by the numbers in the drawings are as follows:

RELATED TECHNOLOGY 10. therapeutic apparatus; 110. treatment head; 112. electrode;

The present application:

12. preset depth; 20. therapeutic apparatus; 201. first area; 203. second area; 202. the first set of electrodes; 204. the second set of electrodes; 206. the third set of electrodes; 21. signal generator; 212. radio frequency signal generator; 214. electrical muscle stimulation signal generator; 22. switch circuit; 220. circuit modulator; 222. switch device; 224. voltage regulator; 23. treatment head; 24. electrode; 242. working electrode; 2422. working positive electrode; 2424. working negative electrode; 244. regulating electrode; 2442. regulating positive electrode; 2444. regulating negative electrode; 25. control unit; 252. temperature sensor; 254. current sensor; 256. voltage sensor.

DETAILED DESCRIPTION OF THE
PREFERRED EMBODIMENT

In order to make the purpose, technical scheme and advantages of the application clearer, the implementation of the application will be further described in detail in combination with the attached drawings.

It should be understood that "multiple" mentioned in the present application refers to two or more. In the description of the application, unless otherwise specified, "/" means or, for example, A/B can mean A or B; The "and/or" in this application is only a description of the association relationship of the associated objects, which means that there can be three kinds of relationships, for example, A and/or B, which can mean that there are three cases: A alone, A and B at the same time, and B alone. In addition, in order to clearly describe the technical scheme of the application, the words "first" and "second" are used to distinguish the same items or similar items with the same functions. Those skilled in the art can understand that the words "first" and "second" do not limit the quantity and execution order, and the words "first" and "second" are not limited to certain differences.

Before explaining the embodiments of the present application in detail, the application scenarios of the embodiments of the present application are explained first.

FIG. 1 is a schematic diagram of the appearance of the therapeutic apparatus in the related technology. Referring to FIG. 1, a plurality of electrodes 112 mounted on the treatment head 110 are usually set in the therapeutic apparatus 10 for the radio frequency treatment. When the therapeutic apparatus 10 is used by the user, the treatment head 110 can be attached to the surface of the skin, thereby a plurality of electrodes 112 is attached to the surface of the skin. At this time, the user's skin is used as a conductor and radio frequency current is applied to the skin through the electrode 112.

In the related technology, during the treatment process, all electrodes 112 of the therapeutic apparatus 10 must be attached to the surface of skin. However, some human skin tissues, such as the face, have complex contours rather than flat surfaces. In the process of using the therapeutic apparatus 10, it is impossible to make all the electrodes 112 attached to the skin surface in the narrow space such as the corner of the eye and the alar of the nose. However, if the surface area of the treatment head 110 for mounting the electrode 112 is reduced, the treatment time will be prolonged and the heat dissipation of the therapeutic apparatus 10 will be unfavorable.

A therapeutic apparatus and a control method thereof is provided in the present application, in which the skin in narrow space can be treated by controlling only part of the electrodes on the treatment head of the therapeutic apparatus to output therapeutic signals. Meanwhile, the treatment time will not be prolonged.

The therapeutic apparatus 20, its control method and storage medium provided by the embodiment of the present application are explained in detail below. In each embodiment of the application, the connection between the two electrical devices refers to an electrical connection. The electrical connection here refers to the transmission of electrical signals between two electrical devices through wired or wireless connection.

It should be understood that the therapeutic apparatus 20 and its control method and storage medium provided by the embodiment of the present application do not need to improve the appearance of the therapeutic apparatus 20. Therefore, the schematic diagram of the appearance as shown in FIG. 1 is still applicable to the therapeutic apparatus 20 provided by the embodiment of the present application.

Figure 2:
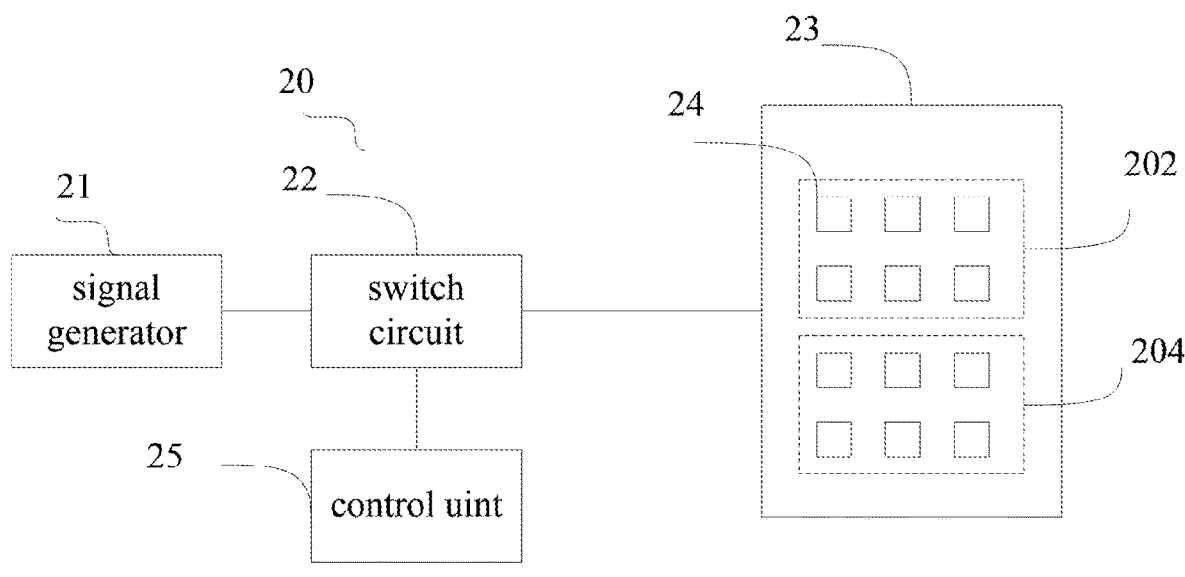
FIG. 2 is a structure diagram of the first therapeutic apparatus provided by the embodiment of the present application.

FIG. 2 is a structure diagram of the first therapeutic apparatus provided by the embodiment of the present application. Referring to FIG. 2, the therapeutic apparatus 20 comprises a signal generator 21 configured for generating a therapeutic signal, a treatment head 23 configured for mounting the electrodes, multiple sets of electrodes, a switch circuit 22 and a control unit 25 connected with the switch circuit 22 and configured for controlling the on-off of the switch circuit 22. In the embodiment of the present application, multiple sets of electrodes are arranged on the treatment head 23 of the therapeutic apparatus 20. The multiple sets of electrodes are connected with the signal generator 21 through the switch circuit 22, and the on-off of the switch circuit 22 is controlled by the control unit 25. When the therapeutic apparatus 20 is working, the switch circuit 22 is controlled by the control unit 25 to make one set or several sets of the multiple sets of electrodes connected with the signal generator 21 to output the therapeutic signal.

The treatment head 23 can be made of insulating material, and its surface can be any one of an arc surface, an annular surface and plane, which is not limited here. The therapeutic apparatus 20 may include only one treatment head 23, or may include two or more treatment heads.

The electrode 24 is made of conductive material and is used to contact the surface of skin tissue, so that when the therapeutic apparatus 20 works, the therapeutic signal is output to the skin tissue through the electrode 24. In the embodiment of the application, the therapeutic apparatus 20 comprises multiple sets of electrodes, and each set of electrodes are composed of one or more electrodes. Each set of electrodes can be called an electrode assembly.

The switch circuit 22 is connected between the signal generator 21 and multiple sets of electrodes for controlling the connection or disconnection of each set of electrodes and the signal generator 21. In the embodiment of the application, the therapeutic apparatus 20 includes one or more switch circuits 22, through which the circuit between each set of electrodes and the signal generator 21 is relatively independent of each other. In other words, through the switch circuit 22, each set of electrodes can be connected or disconnected from the signal generator 21 without being affected by other sets of electrodes. Multiple electrodes 24 in each set of electrodes can be controlled to connect or disconnect with the signal generator 21 at the same time, or each electrode 24 can be controlled to connect or disconnect with the signal generator 21 independently.

When the therapeutic apparatus 20 provided by the embodiment of the application is used on the flat skin surface, the control unit 25 can control multiple sets of electrodes to be connected with the signal generator 21 through the switch circuit 22, so that all the electrodes 24 on the treatment head 23 can output therapeutic signals.

When the therapeutic apparatus 20 provided by the embodiment of the application is applied in the narrow space such as the corner of the eye and the alar of the nose, the control unit 25 control only one or more than two sets of electrodes to be connected with the signal generator 21 through the switch circuit 22 to output the therapeutic signal. At this time, the area of the electrode assembly which outputs the therapeutic signal is small, so it is easy to be attached to the surface of the skin in the narrow space to treat the skin in the narrow space. At the same time, when only one set or more than two sets of electrodes are connected with the signal generator 21, the output power of the signal generator 21 can be concentrated in the connected electrode assembly, so as to improve the treatment efficiency and shorten the treatment time.

Figure 3:
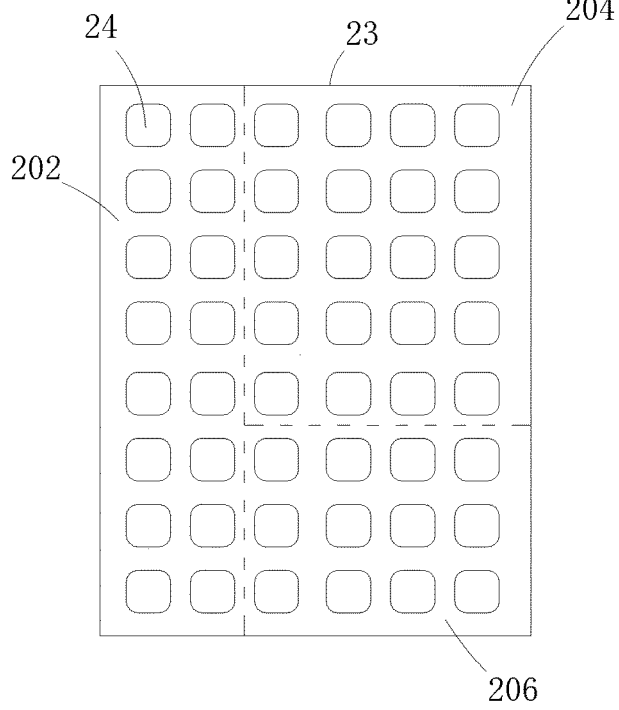
FIG. 3 is a schematic diagram of the first electrode grouping mode provided by the embodiment of the present application.
Figure 4:
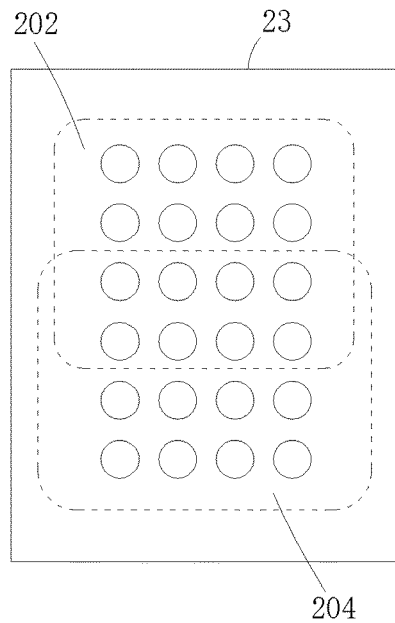
FIG. 4 is a schematic diagram of the second electrode grouping mode provided by the embodiment of the present application.

FIG. 3 and FIG. 4 show different grouping modes of electrodes 24 in the embodiment of the present application. Any two sets of electrodes among the multiple sets of electrodes are completely different, which means that there is no electrode sharing phenomenon in any two sets of electrodes. As shown in FIG. 3, all the electrodes 24 on the treatment head 23 are divided into a first electrode assembly 202, a second electrode assembly 204 and a third electrode assembly 206. No electrode is sharing between the first electrode assembly 202 and the second electrode assembly 204; no electrode is sharing between the second electrode assembly 204 and the third electrode assembly 206; no electrode is sharing between the third electrode assembly 206 and the first electrode assembly 202. The sharing of electrodes between two sets of electrodes in the multiple sets means that some of the electrodes 24 will belong to two electrode assemblies at the same time. As shown in FIG. 4, all the electrodes 24 on the treatment head 23 are divided into a first electrode assembly 202 and a second electrode assembly 204. The two rows of electrodes 24 near the bottom of the first electrode assembly 202 are also belong to the second electrode assembly 204. The bottom here refers to the direction relative to the paper. In the embodiment of the application, the two sets of electrodes in the multiple sets share part of the electrodes, which can make the division mode of the electrode assembly more flexible, so as to adapt to the different use requirements of the user for the therapeutic apparatus.

Figure 5:
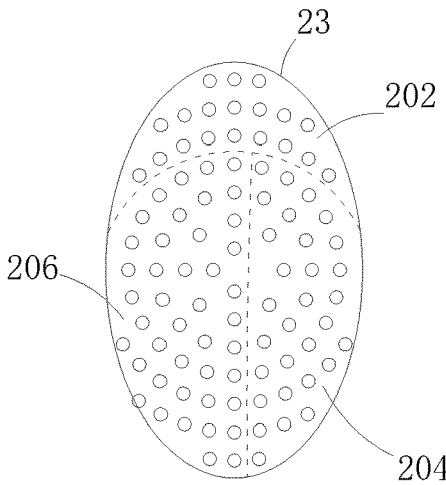
FIG. 5 is a schematic diagram of the third electrode grouping mode provided by the embodiment of the present application.

The electrodes 24 may be arranged regularly within the treatment head 23, as shown in FIGS. 3 and 4. The electrodes 24 may also be irregularly arranged in the treatment head 23, as shown in FIG. 5. In general, on the premise that there is a certain interval between the two adjacent electrodes 24, the electrodes 24 arranged in the treatment head 23 can be arranged as closely as possible, so as to improve the therapeutic signal output ability of the treatment head 23. Of course, the electrodes 24 in the treatment head 23 can also be arranged irregularly according to the treatment requirements.

The electrode 24 may be shaped in a rectangle, a rectangle with a fillet as shown in FIG. 3, or a circle, a ring, a crescent or a triangle. The sizes of different electrodes 24 can be equal or unequal, and are not limited in the embodiment of the present application.

Please continue to refer to FIG. 3 and FIG. 5. In the embodiment of the present application, the treatment head 23 may be divided into a plurality of areas, at least two of which are different in shape, and each area is used to set a set of electrodes. In the embodiment of the application, by defining that multiple sets of electrodes are located in a plurality of areas one by one, and the shapes of at least two areas are different, the electrodes of each set can form different shapes, so that the different electrode assemblies can adapt to the skin surfaces at different positions. At this time, when the therapeutic apparatus 20 treats the skin tissue surface in the narrow space, different electrode assemblies can be selected to output the therapeutic signal according to the shape of the narrow space.

In the embodiment of the present application, multiple sets of electrodes are divided into working electrodes 242 and regulating electrodes 244. The regulating electrodes 244 are configured for adjusting the magnitude and direction of the electric field formed by the working electrodes 242.

Figure 6:
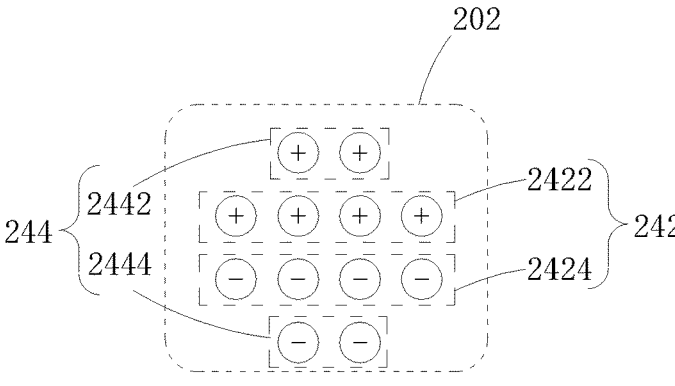
FIG. 6 is a schematic diagram of the first arrangement of the electrode provided by the embodiment of the present application.
Figure 7:
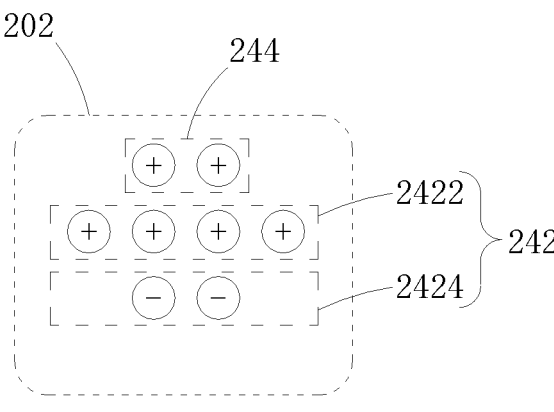
FIG. 7 is a schematic diagram of the second arrangement of the electrode provided by the embodiment of the present application.
Figure 8:
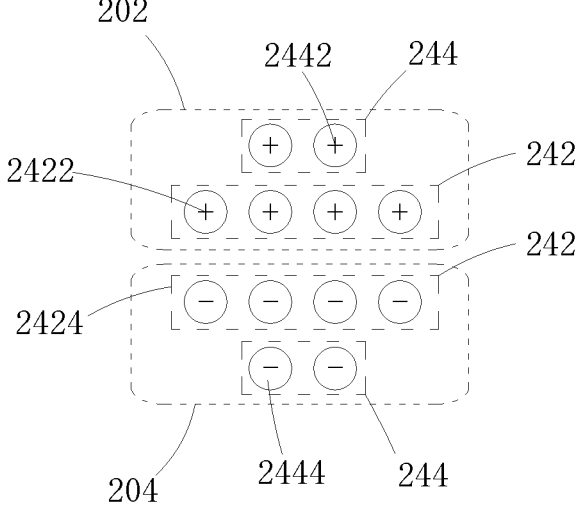
FIG. 8 is a schematic diagram of the third arrangement of the electrode provided by the embodiment of the present application.

FIGS. 6 to 8 show the arrangement of different electrodes 24 in the embodiment of the present application. Refer to FIG. 6 and FIG. 7, the first electrode assembly 202 is taken as an example. In the first electrode assembly 202, the working electrodes 242 include a working positive electrode 2422 and a working negative electrode 2424; the regulating electrodes 244 include at least one of a regulating positive electrode 2442 and a regulating negative electrode 2444. In other embodiments of the application (for example, FIG. 8), one set of electrodes include working electrodes 242 and regulating electrodes 244, and the working electrodes 242 include a working positive electrode 2422 or a working negative electrode 2424. The polarities of the regulating electrode 244 and the working electrode 242 are the same.

Generally, as shown in FIG. 6 to FIG. 8, for a set of electrodes, the number of positive electrodes and negative electrodes can be the same or different. For treatment head 23 of therapeutic apparatus 20, the number of positive electrodes and negative electrodes of all electrodes 24 in the treatment head 23 is generally the same.

Figure 9:
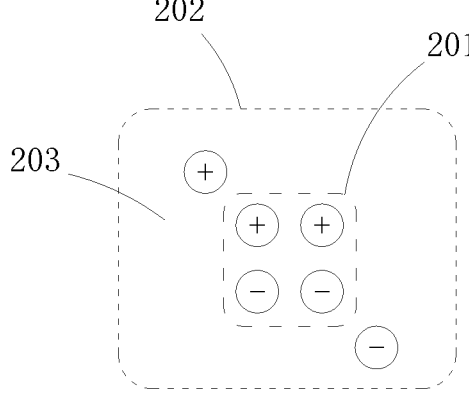
FIG. 9 is a schematic diagram of the first position relationship of the electrode provided by the embodiment of the present application.
Figure 10:
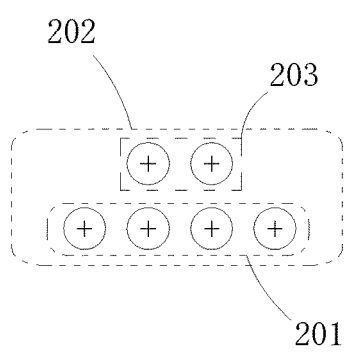
FIG. 10 is a schematic diagram of the second position relationship of the electrode provided by the embodiment of the present application.

Please refer to FIG. 9 and FIG. 10. In the embodiment of the present application, one set of electrodes include working electrodes 242 and regulating electrodes 244. The treatment head 23 is divided into a first area 201 and a second area 203 (the area outside of the area 201), and the first area 201 and the second area 203 do not overlap each other. The working electrodes 242 are located in the first area 201, and the regulating electrodes 244 are located in the second area 203, so that the working electrodes 242 and the regulating electrodes 244 do not cross each other. The second area 203 can surround the first area 201. As shown in FIG. 9, when the working positive electrodes 2422 and working negative electrodes 2424 are arranged in the first area 201 has, the regulating electrodes 244 surrounds the working electrodes 242 in the first area 201 to adjust the electric field formed by the working electrodes 242 in the first area 201. Alternatively, the second area 203 may be arranged on one side of the first area 201, as shown in FIG. 10. In other words, in the application embodiment, the regulating electrodes 244 are arranged at the periphery of the area in which the working electrodes 242 are located, so as to adjust the size and direction of the electric field formed by the working electrodes 242.

It needs to be understood that in this embodiment of the present application, the definition of the regulating electrodes 244 and the working electrodes 242 is not absolute, but relative, and the positive and negative nature of the regulating electrodes 244 can be changed. The function of the regulating electrodes 244 will be further described in detail with reference to FIG. 11 to FIG. 16. Among them, FIG. 12, FIG. 14 and FIG. 16 show the effect of electrode 24 when a set of electrodes are attached to the surface of skin tissue. The direction shown in the figure is perpendicular to the plane of the skin tissue surface. Among them, the working positive electrode 2422, the working negative electrode 2424, the regulating positive electrode 2442 and the regulating negative electrode 2444 are attached to the skin tissue surface. The solid line with an arrow shows the electric field formed by electrodes 24 in the skin tissue. Label 12 represents the preset depth in the skin tissue. In FIG. 12, FIG. 14 and FIG. 16, the preset depth is the same.

As shown in FIG. 11 to FIG. 16, a voltage signal is applied to each electrode 24. The voltage of the working positive electrodes 2422 is $X_1 \sin (2*\pi*f_1*t+\theta_1)$, X1 represents the amplitude of the voltage of the working positive electrodes 2422, $f_1$ represents the frequency of the working positive electrodes 2422, t is the working time, and $\theta_1$ is the phase angle. The voltage of the working negative electrodes 2424 is $X_2 \sin (2*\pi*f_2*t+\theta_2)$, $X_2$ is the amplitude of the voltage of the working negative electrodes 2424, $f_2$ is the frequency of the working positive electrodes 2422, t is the working time, and $\theta_2$ is the phase angle. The voltage of the regulating positive electrode 2442 is $X_3 \sin (2*\pi*f_3*t+\theta_3)$, $X_3$ is the amplitude of the voltage of the regulating positive electrodes 2442, $f_3$ is the frequency of the regulating positive electrode 2442, t is the working time, and $\theta_3$ is the phase angle. The voltage of the regulating negative electrodes 2444 is $X_4 \sin (2*\pi*f_4*t+\theta_4)$, $X_4$ is the amplitude of the voltage of the regulating positive electrodes 2442, $f_4$ is the frequency of the regulating positive electrodes 2442, t is the working time and $\theta_4$ is the phase angle. In general, $f_1$, $f_2$, $f_3$ and $f_4$ can be between 0.1 Hz and 10 MHz. In the examples of FIGS. 11 to 16, $f_1$, $f_2$, $f_3$ and $f_4$ are all set to be 1 MHz; the amplitude of the voltage is the same ($X_1=X_2=X_3=X_4=10V$), but the working negative electrode has a difference phase angle of $\pi$, i.e $\theta_1=\theta_2=\theta_3=\theta_4+\pi$. A phase angle of $\pi$ represents an opposite polarity. $X_4 \sin(2*\pi*f_4*t+\pi)=(-X_4)\sin(2*\pi*f_4*t)$. For simplicity, we can use $(-X_4)$ as the amplitude, which is a negative value.

Figure 11:
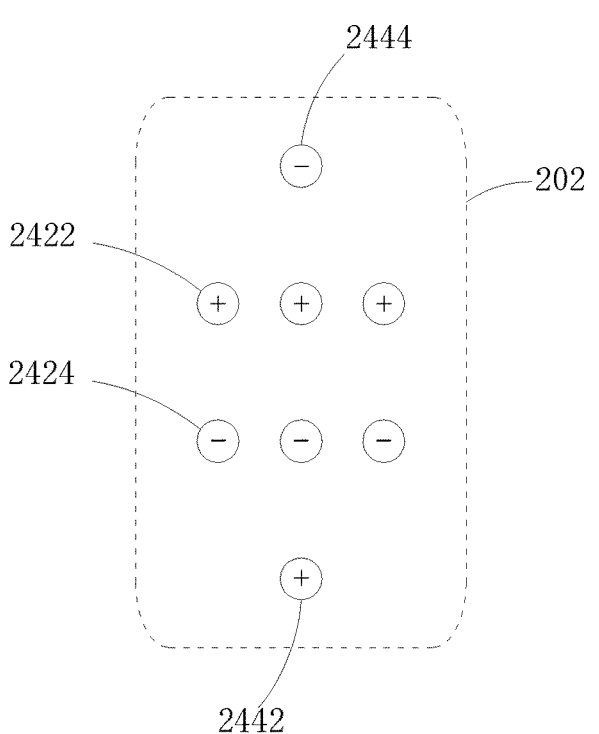
FIG. 11 is a schematic diagram of the third position relationship of the electrode provided by the embodiment of the present application.
Figure 12:
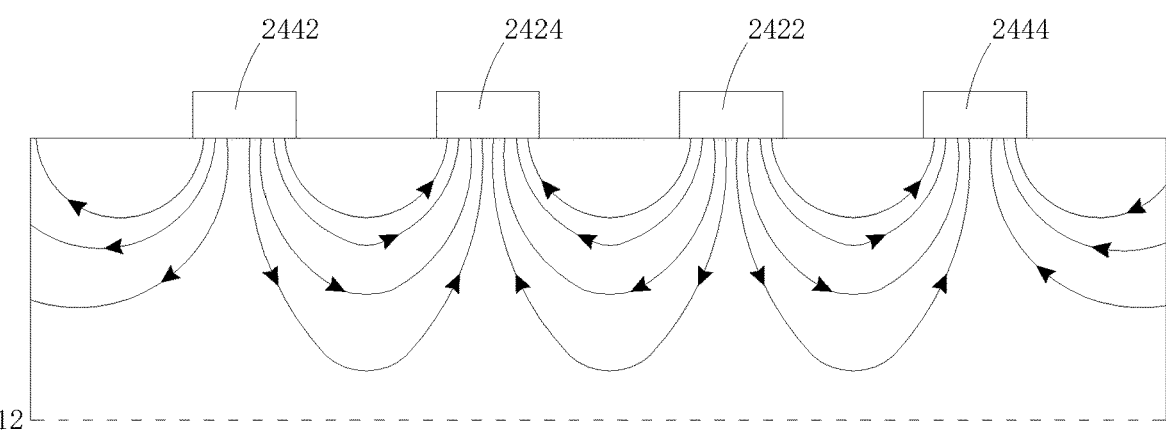
FIG. 12 is a schematic diagram of the first effect of the electrode provided by the embodiment of the present application.

Referring to FIGS. 11 and 12. Relative to the paper surface, the direction from left to right in FIG. 12 is the direction from bottom to top in FIG. 11. In the example of FIGS. 11 and 12, the amplitude of the voltage of the regulating positive electrodes 2442 is 10V, and the amplitude of the voltage of the regulating negative electrodes 2444 is −10V. It can be seen from FIG. 12 that the electric field formed by the electrodes 24 does not reach the preset depth due to the dispersing effect of the regulating electrodes 244 on the electric field formed by the working electrodes 242. At this time, the therapeutic apparatus 20 is suitable for the treatment of superficial layer of the skin tissue.

Figure 13:
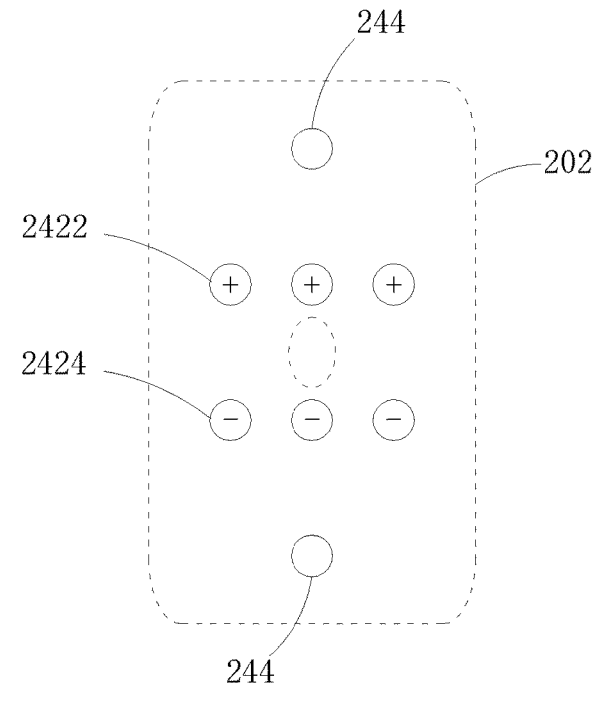
FIG. 13 is a schematic diagram of the fourth position relationship of the electrode provided by the embodiment of the present application.
Figure 14:
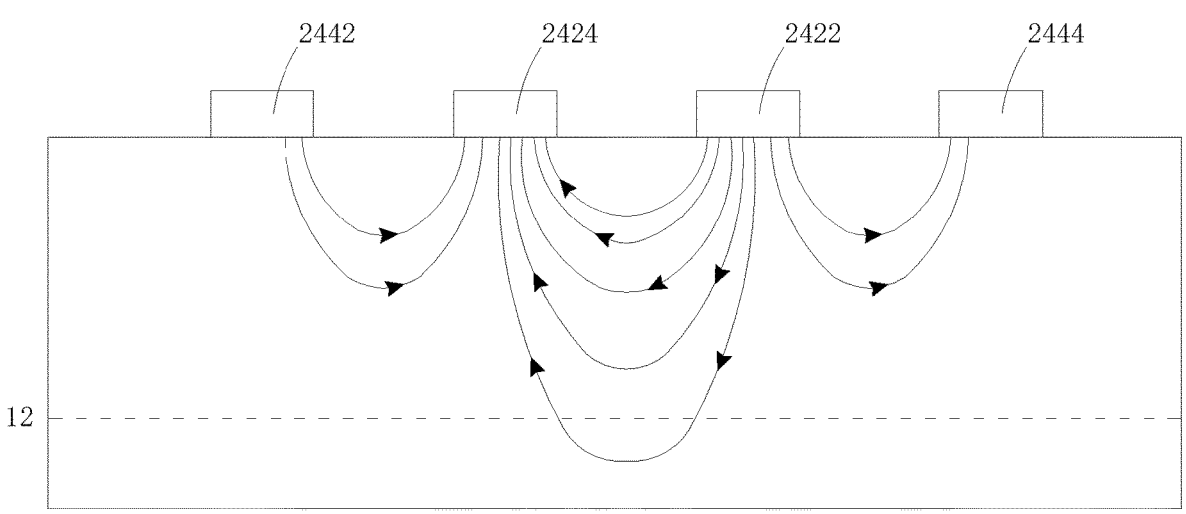
FIG. 14 is a schematic diagram of the second effect of the electrode provided by the embodiment of the present application.

Referring to FIGS. 13 and 14. Relative to the paper surface, the direction from left to right in FIG. 14 is the direction from bottom to top in FIG. 13. In the examples of Referring to FIGS. 13 and 14, no voltage is applied on the regulating electrodes 244. As can be seen from FIG. 14, since the electric field formed by the working electrodes 242 is not dispersed or strengthened by the regulating electrodes 244, the electric field formed by the electrodes 24 reaches a preset depth. The size range of the electric field formed by the electrodes 24 at the preset depth is shown in the dotted line ellipse in FIG. 13.

Figure 15:
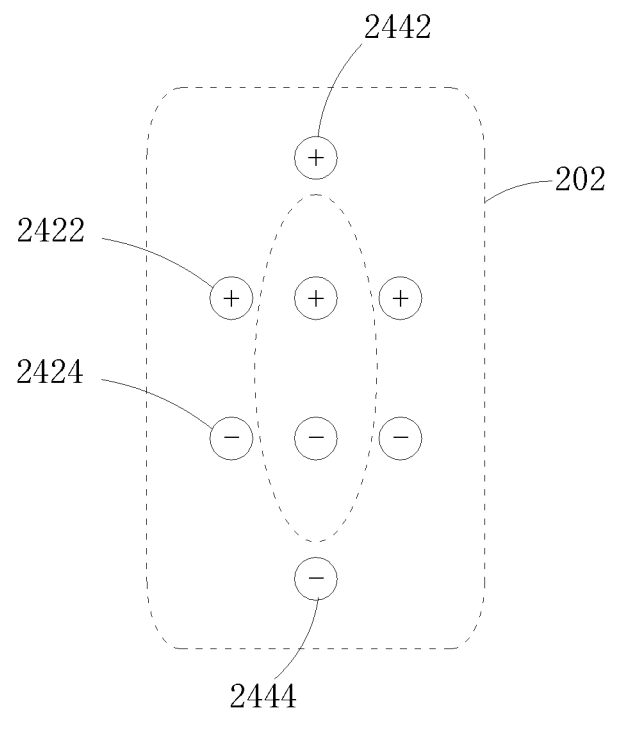
FIG. 15 is a schematic diagram of the fifth position relationship of the electrode provided by the embodiment of the present application.
Figure 16:
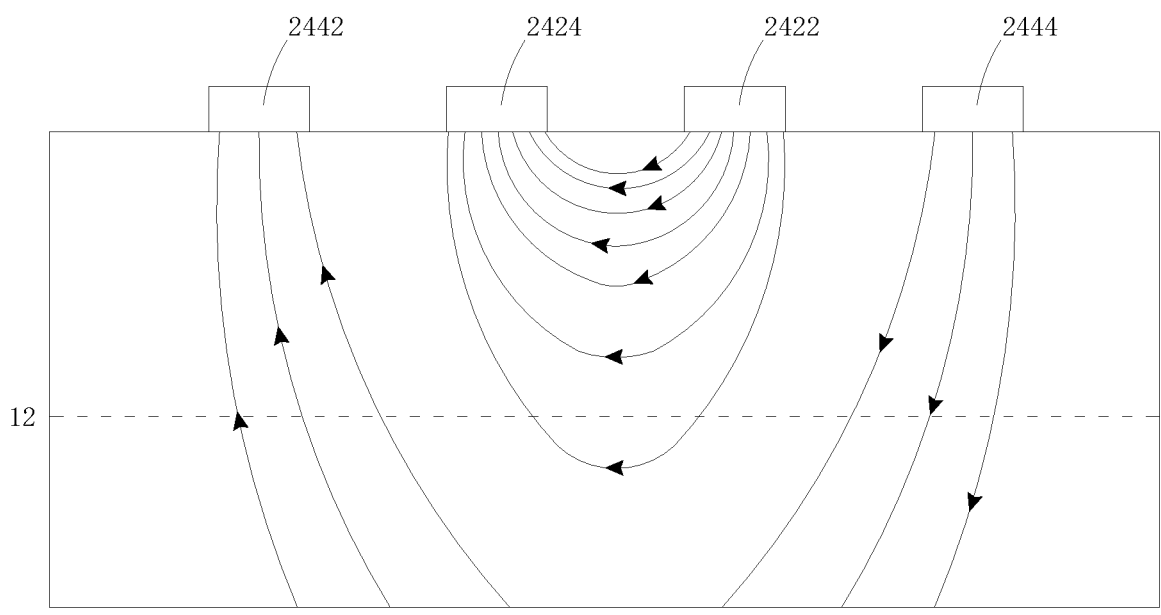
FIG. 16 is a schematic diagram of the third effect of the electrode provided by the embodiment of the present application.

Referring to FIGS. 15 and 16. With respect to the paper surface, the direction of FIG. 16 from left to right is the direction of FIG. 15 from downward to upward. In the example of FIGS. 15 and 16, the amplitude of the voltage of the regulating positive electrodes 2442 is 15V, and the amplitude of the voltage of the regulating negative electrodes 2444 is −10V. It can be seen from FIG. 16 that the electric field formed by electrodes 24 reaches a preset depth due to the strengthening effect of the regulating electrodes 244 on the electric field formed by the working electrodes 242. The magnitude range of the electric field formed by electrodes 24 at a preset depth is shown in the dotted ellipse in FIG. 15. At this time, the therapeutic apparatus 20 is suitable for the treatment of deep skin tissue.

The therapeutic apparatus 20 provided by the embodiment of the application can dynamically adjust the depth distribution of the therapeutic signal output by the electrodes 24 by the regulating electrodes 244, so as to make the therapeutic apparatus 20 more applicable.

Figure 17:
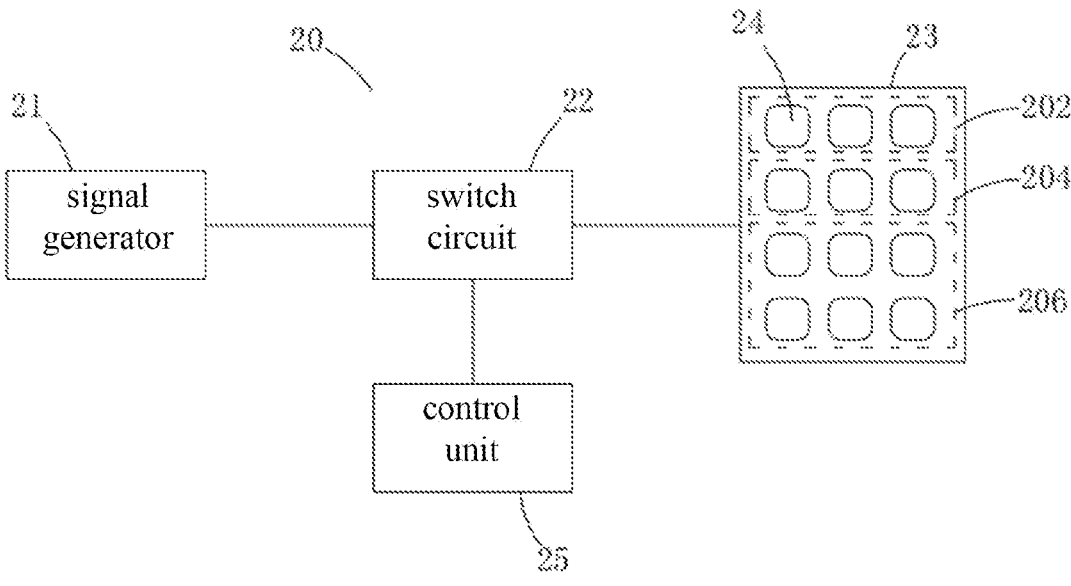
FIG. 17 is a structure diagram of the second therapeutic apparatus provided by the embodiment of the present application.
Figure 18:
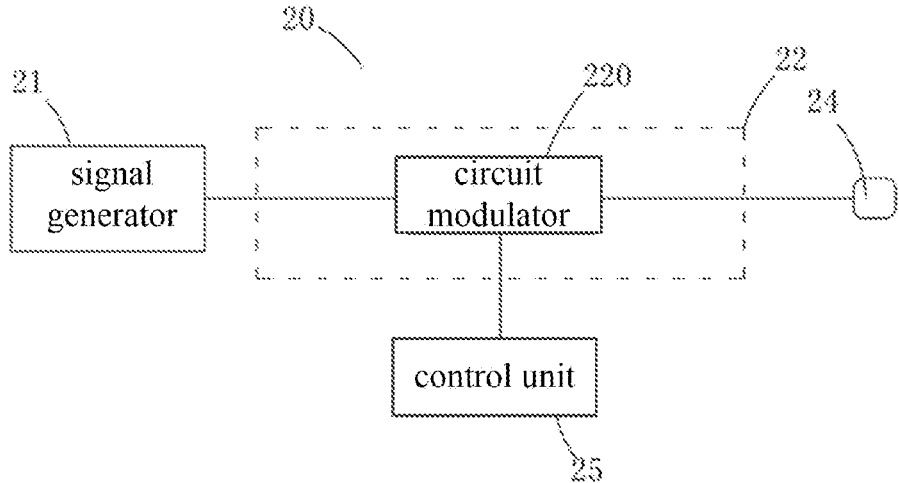
FIG. 18 is a schematic diagram of the first circuit connection provided by the embodiment of the present application.

The following describes an implementation method of adjusting the voltage of the regulating electrodes 244 in combination with the drawings. Please referring to FIG. 17, which is a structure diagram of the therapeutic apparatus 20 provided by the embodiment of the present application. Taking one electrode 24 as an example, FIG. 18 shows the schematic diagram of its circuit connection. Referring to FIG. 18, the switching circuit 22 may include a circuit modulator 220. The circuit modulator 220 is connected between the signal generator 21 and the electrode 24. The circuit modulator 220 is connected with the control unit 25. The opening and closing of the circuit modulator 220 is controlled by the control unit 25, and the voltage of the electrode connected to the circuit modulator 220 is modulated through the circuit modulator 220.

Figure 19:
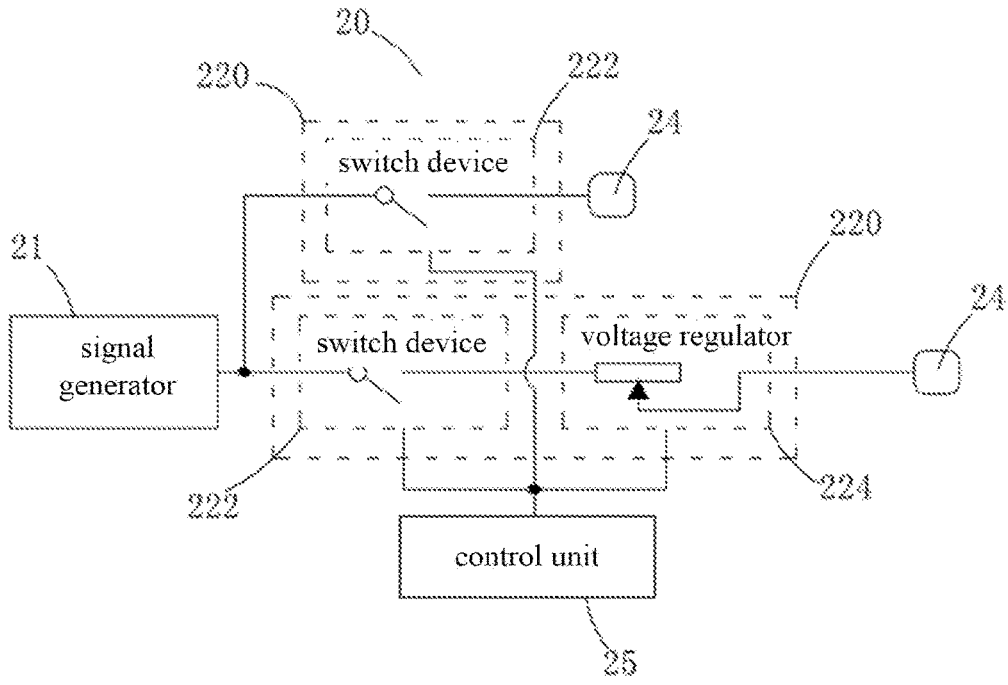
FIG. 19 is a schematic diagram of the second circuit connection provided by the embodiment of the present application.

Referring to FIG. 19, the circuit modulator 220 may include a switching device 222 and a voltage regulator 224. The switching device 222 and the voltage regulator 224 which are connected in series are connected between the signal generator 21 and the electrode 24. The switching device 222 and the voltage regulator 224 are both connected with the control unit 25. The control unit 25 is used to control the opening and closing of the switching device 222, and modulates the voltage of the connected electrode 24 through the voltage regulator 224 when the switching device 222 is closed.

It should be understood that the switching device 222 and the voltage regulator 224 in FIG. 19 are connected in series, but this should not be limited. The voltage regulator 224 and the switching device 222 can also be a voltage adjustable switching device, and the voltage can be regulated by the modulation signal of the control unit 25.

It is to be understood that in the above embodiments, the circuit modulator 220 including the switch device 222 and the voltage regulator 224 may adjust the voltage of the electrode 24 connected to it. The circuit modulator 220 can be connected between the regulating electrodes 244 and the signal generator 21, or between the working electrodes 242 and the signal generator 21. In other words, during the operation of the therapeutic apparatus 20, the control unit 25 can adjust the voltage of the regulating electrodes 244 through the voltage regulator 224 in the circuit modulator 220, and can also adjust the voltage of the working electrodes 242 through the voltage regulator 224 in the circuit modulator 220. When the voltage amplitude of the working electrodes 242 and the regulating electrodes 224 can be adjusted, the adjustment range of the depth of the therapeutic signal input into the skin tissue can be further increased.

In the embodiment of the present application, referring to FIG. 19, the circuit modulator 220 may include only the switching device 222. At this time, the circuit modulator 220 is only used to control the on-off of the circuit between the electrode 24 or one electrode assembly and the signal generator 21. As shown in FIG. 19, one electrode 24 is connected to the signal generator 21 through a circuit modulator 220 including only a switching device 222. The electrode 24 can be a working electrode 242 or an electrode assembly.

In the embodiment of the present application, the signal generator 21 includes a radio frequency signal generator 212 or/and an electrical muscle stimulation (EMS) signal generator 214.

Figure 20:
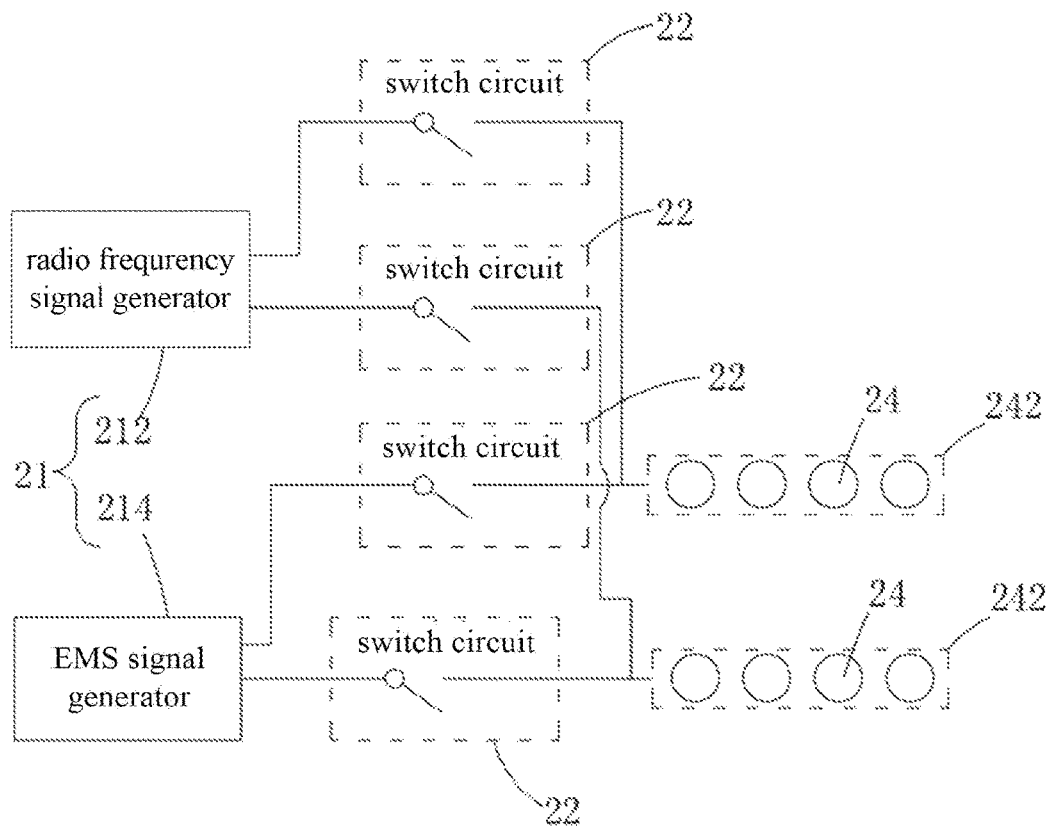
FIG. 20 is a schematic diagram of the fourth circuit connection provided by the embodiment of the present application.

Referring to FIG. 20, the RF signal generator 212 and the EMS signal generator 214 can be respectively connected to one set of electrodes through the switch circuit 22, or simultaneously connected to one set of electrodes through the switch circuit 22. Of course, the RF signal generator 212 and the EMS signal generator 214 can be respectively connected to one electrode 24 through the switch circuit 22, or can be simultaneously connected to one electrode 24 through the switch circuit 22.

When the electrode is only connected with one of the RF signal generators 212 and the EMS signal generator 214 through the switch circuit 22, the electrode can output only one of the EMS signal and the RF signal. Conversely, when the electrode is simultaneously connected with the RF signal generator 212 and the EMS signal generator 214 through the switch circuit 22, the electrode can output both the EMS signal and the RF signal.

In the embodiment of the present application, the signal waveform output by the electrode 24 can also be controlled by controlling the circuit modulator 220 in the switch circuit 22. The electrode 24 can only output the EMS signal or the RF signal, or alternatively output the EMS signal and the RF signal. The waveform of the therapeutic signal output by the electrode 24 can be any one or more of a sine wave, a square wave and a triangular wave.

Figure 21:
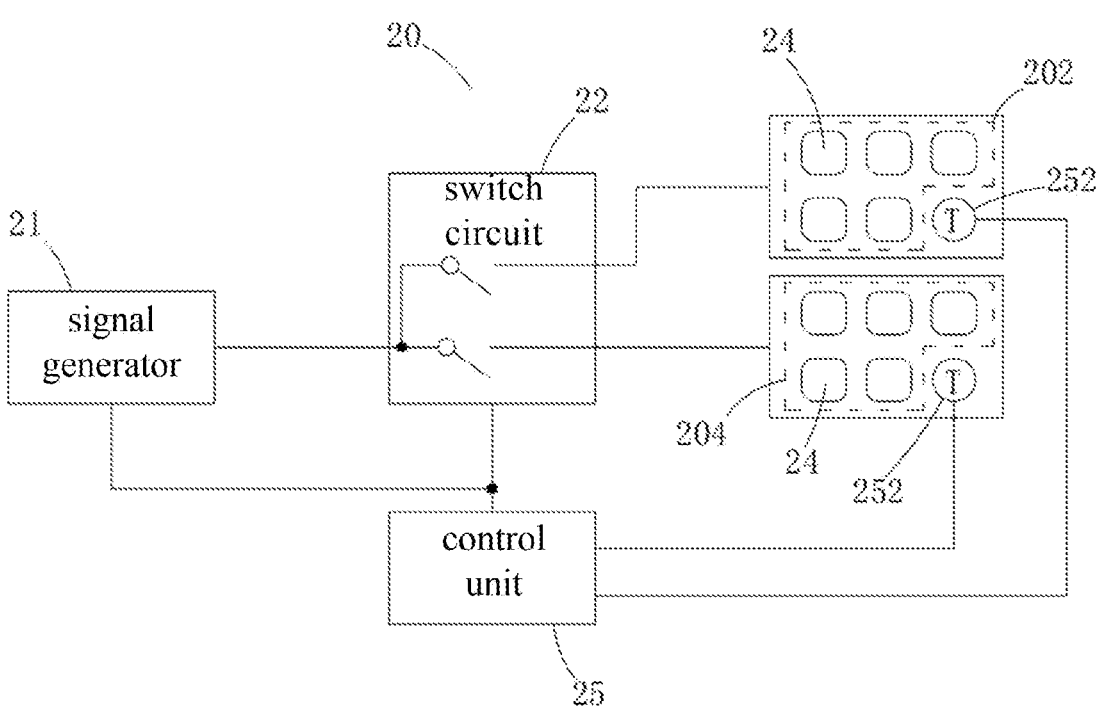
FIG. 21 is a schematic diagram of the fifth circuit connection provided by the embodiment of the present application.

In the embodiment of the present application, the therapeutic apparatus 20 also includes a temperature sensor 252 for detecting a temperature signal. Referring to FIG. 21, the temperature sensor 252 can be set in one set of electrodes, or the temperature sensor 252 can be respectively set in more than two sets of electrodes. The temperature sensor 252 is connected with the control unit 25 and transmits the temperature signal to the control unit 25 after detecting the temperature signal. In the embodiment of the application, the temperature sensor 252 can be a thermistor, an infrared thermometer, a thermocouple, etc.

Figure 22:
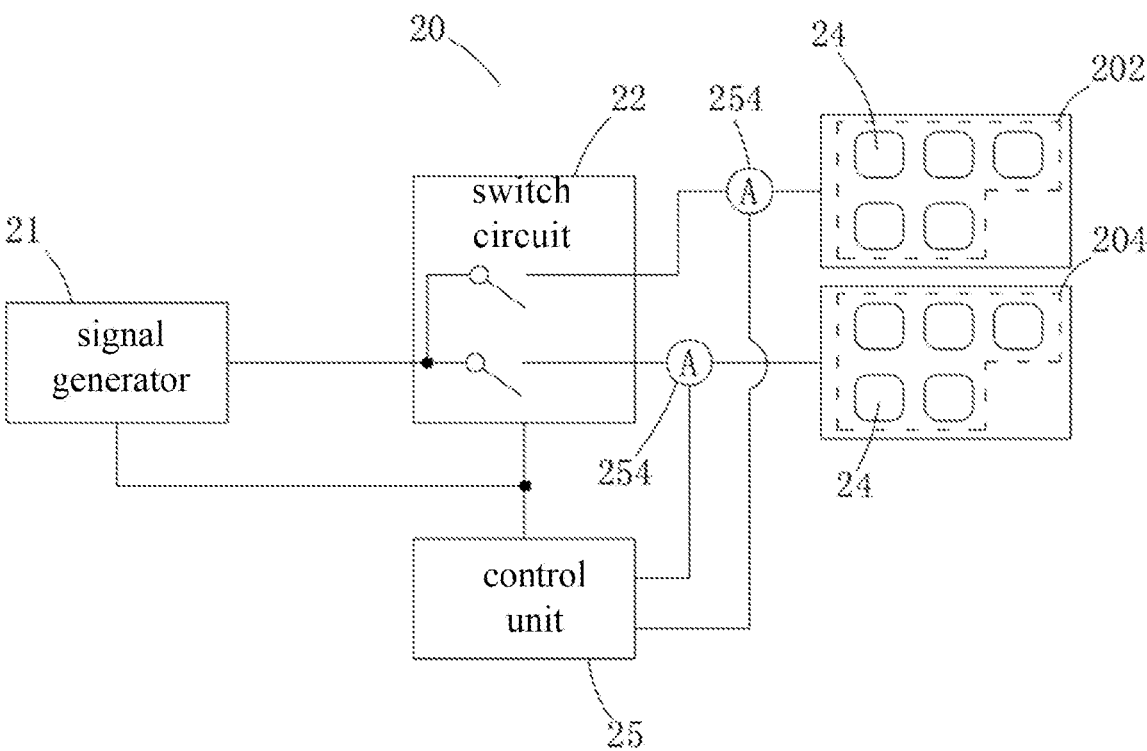
FIG. 22 is a schematic diagram of the sixth circuit connection provided by the embodiment of the present application.

In the embodiment of the present application, the therapeutic apparatus 20 also includes a current sensor 254 for detecting a current signal. As shown in FIG. 22, a current sensor 254 can be connected in series with one set of electrodes, or two or more sets of electrodes can be connected in series with one current sensor 254. The current sensor 254 is connected with the control unit 25 to transmit the current signal to the control unit 25 after the current signal is detected. In the embodiment of the present application, the current sensor 254 may be an electronic ammeter or the like.

Figure 23:
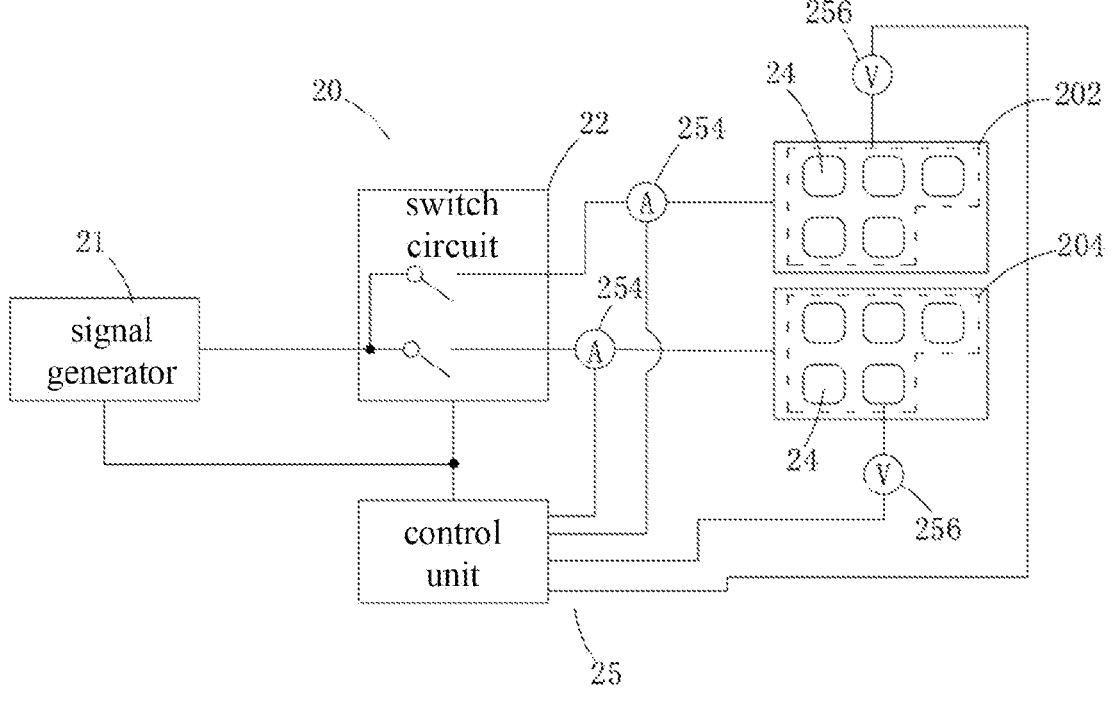
FIG. 23 is a schematic diagram of the seventh circuit connection provided by the embodiment of the present application.

Furthermore, in the embodiment of the present application, the therapeutic apparatus 20 also includes a voltage sensor 256 for detecting a voltage signal. As shown in FIG. 23, the therapeutic apparatus 20 may include a voltage sensor 256 and a current sensor 254. In the embodiment of the application, one set of electrodes can be connected in parallel with the voltage sensor 256, or more than two sets of electrodes can be connected in parallel with one voltage sensor 256 respectively. The voltage sensor 256 is connected with the control unit 25 to transmit the voltage signal to the control unit 25 after detecting the voltage signal. In the embodiment of the application, the voltage sensor 256 can be an electronic voltmeter, an ADC (analog signal converter), a coil inductor, etc.

In the embodiment of the present application, the therapeutic apparatus 20 also includes a speed sensor connected with the control unit 25 for detecting the speed signal. The speed sensor can be set in the therapeutic apparatus. The speed signal is used to characterize the relative movement speed of the therapeutic apparatus and skin tissue. In this embodiment, the speed information can be extracted from the current sensor, the voltage sensor or the impedance data. When the electrode moves rapidly, the current, the voltage or the impedance on the electrode will change rapidly with the change of the skin condition. According to the data, the movement of the treatment head can be judged. In more complex applications, the speed sensor can also be a gyroscope integrated into the therapeutic apparatus.

In the embodiment of the present application, the therapeutic apparatus 20 may also include a detecting sensor connected with the control unit 25 for detecting whether each electrode is in a working state. The working state here means that there is current passing through the electrode, that is, the electrode 24 is in the current loop, or the magnitude of the current is detected to determine the degree of adhesion between the electrode and the skin.

The control method of the above therapeutic apparatus 20 is described below.

Figure 24:
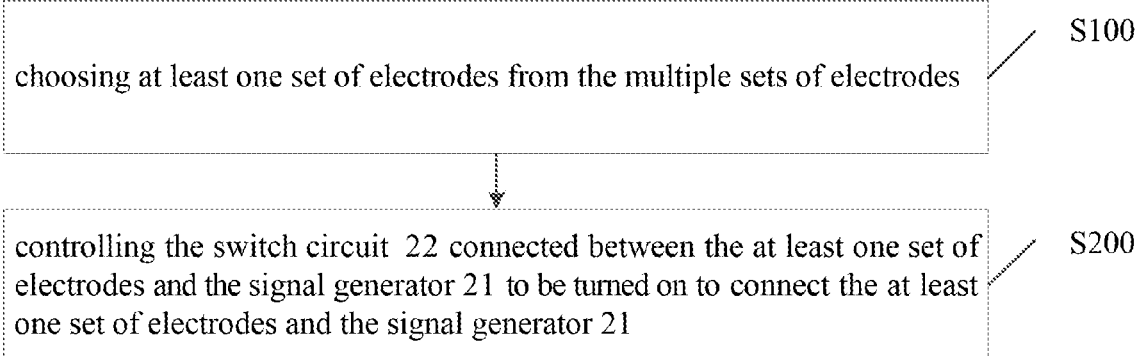
FIG. 24 is a flow chart of the first control method provided by the embodiment of the present application.

FIG. 24 is the flow chart of the control method of the therapeutic apparatus provided by the embodiment of the present application, which is applied to the control unit 25 of the therapeutic apparatus 20 as shown in FIG. 2. Referring to FIG. 24, the control method of the therapeutic apparatus provided by the embodiment of the present application comprises the following steps:

S100, choosing at least one set of electrodes from the multiple sets of electrodes.

S200, controlling the switch circuit 22 connected between the at least one set of electrodes and the signal generator 21 to be turned on to connect the at least one set of electrodes and the signal generator 21.

In the embodiment of the present application, when the therapeutic apparatus 20 is in operation, according to the instructions entered by the user, at least one set of electrodes can be chosen from the multiple sets of electrodes by the control unit 25. The switch circuit 22 can also be controlled by the control unit 25, making the at least one set of electrodes chosen in the step S100 to be connected with the signal generator 21. Meanwhile, the therapeutic signal is outputted by the at least one set of electrodes chosen in step S100. The electrode assembly which are not chosen in the step S100 can not be connected with signal generator 21 through the switch circuit 22, thus can not output the therapeutic signal.

In the embodiment of the present application, the electrodes 24 on the treatment head 23 are divided into a plurality of electrode assemblies. When the control method is executed by the control unit 25, only part of the electrode assemblies in the multiple sets of electrodes can be controlled to output the therapeutic signal. At this time, the area of the electrode assemblies outputting the therapeutic signal is small, so it is convenient to adhere to the surface of the skin tissue in the narrow space and treat the skin tissue in the narrow space. At the same time, since only part of the electrode assemblies are connected with the signal generator 21, the output power of the signal generator 21 can be concentrated on the electrode assemblies connected with it, so as to improve the treatment efficiency of skin tissue in a narrow space and shorten the treatment time.

Referring to FIG. 25, in the embodiment of the present application, before the above step S100, the control method of the application further comprises the following step:

S001, if a first control instruction is detected, dividing all the electrodes 24 of the therapeutic apparatus into multiple sets of electrodes according to a grouping mode indicated by the first control instruction.

In the embodiment of the application, when the electrodes 24 on the treatment head 23 are grouped to form multiple sets of electrodes, there can be a variety of different grouping modes according to different needs.

For example, in some embodiments of the present application, more than two areas are arranged on the treatment head 23, each of which is used to set a set of electrodes. When the therapeutic apparatus 20 is applied to the skin tissue surface in the narrow space, different electrode assemblies are chosen by the control unit 25 to output the therapeutic signal according to the shape of the narrow space. In other words, this electrode grouping mode groups the electrodes 24 according to the shapes of different areas on the treatment head 23.

For example, in other embodiments of the present application, the signal generator 21 includes a radio frequency signal generator 212 and an EMS signal generator 214, and the electrodes 24 are divided into multiple sets of electrodes to output different types of therapeutic signals. For example, as shown in FIG. 3, all electrodes 24 on the treatment head 23 are divided into a first electrode assembly 202, a second electrode assembly 204 and a third electrode assembly 206. After grouping, the first electrode assembly 202 can only communicate with the EMS signal generator 214 through the switch circuit 22 for outputting the EMS signal; The second electrode group 204 can only be connected with the RF signal generator 212 through the switch circuit 22 for outputting RF signals; the third electrode assembly 206 can be connected with both the EMS signal generator 214 and the radio frequency signal generator 212 through the switch circuit 22, and is used to output the EMS signal and the radio frequency signal. In other words, this electrode grouping mode groups the electrodes 24 according to the type of output therapeutic signal.

For example, in other embodiments of the present application, during the initiation and operation of the electrodes, the signals output by the signal generator at a single time are output only to one or several of a plurality of areas (less than the total number of partitions). The output power of RF signal generator is closed related to the load. If all electrodes are connected, the load is too large, making total RF output power deviating from the optimization state too much, and the efficiency is very poor. Only when the load is in a certain range, the efficiency of the signal generator can maintain high and a large power can be output. The output load can be controlled in a certain range by grouping, to optimize the output. For a single area, the signal strength of the received RF signal is directly proportional to the treatment effect. At the same time, the skin can be prevented from generating excessive heat because of a short output pause of each area. Therefore, the load matching can be adjusted by grouping to improve the output efficiency, and ensure that each partition can obtain high energy output.

For example, in other embodiments of the present application, the electrodes 24 may be grouped according to the user's usage habits. In this grouping mode, the electrodes 24 can be divided into a plurality of electrode assemblies according to the user's habit of using the therapeutic apparatus 20. This division process will be described in detail in the next embodiment.

In the embodiment of the present application, a variety of grouping modes may be stored in the control unit 25 in advance, which activate the grouping settings by control instructions. When the therapeutic apparatus 20 is used, the first control instruction can be automatically triggered through external operations, such as a click operation, a sliding operation, a voice operation, a gesture operation, or somatosensory operation, or using changes in environmental conditions (such as skin fit). The first control instruction is used to specify one of a variety of grouping modes. When the first control instruction triggered by the user is detected the control unit 25, all electrodes 24 of the therapeutic apparatus 20 are divided into multiple sets of electrodes according to the grouping mode specified by the first control instruction.

It should be noted that in the embodiment of the present application, the method of grouping the electrodes 24 according to the type of the output therapeutic signal can be combined with the method of grouping the electrodes 24 according to the shape of different areas on the treatment head 23. That is, after grouping the electrodes 24 according to the shape of different areas on the treatment head 23, each electrode assembly can also output at least one of the EMS signal and the RF signal. Similarly, the method of grouping the electrodes 24 according to the type of the output therapeutic signal can also be combined with the method of grouping the electrodes 24 according to the user's usage habits. That is, after grouping the electrodes 24 according to the user's usage habits, each electrode assembly can also output at least one of the EMS signal and the RF signal.

The operation of grouping the electrodes 24 according to the user's usage habits is described below. Refer to FIG. 26, the following steps S01 to S03 can be included.

In the embodiment of the present application, a detecting sensor connected to the control unit 25 is further included in the therapeutic apparatus 20, and is configured for detecting the presence of a current at each electrode 24 of multiple sets of electrodes.

S01, the switch circuits 22 between all the electrodes 24 and the signal generator 21 are controlled to be turned on, making all the electrodes 24 in the treatment head 23 connected with the signal generator 21 to output the therapeutic signal.

S02, detecting sensing signals by the detecting sensor and determining a usage of all electrodes 24 in the treatment head 23 according to the detected sensing signals.

The detecting sensor here may be a current sensor 254 or a temperature sensor 252, or a combination of a current sensor 254 and a voltage sensor 256. Each electrode 24 is correspondingly provided with a detecting sensor.

When the detecting sensor is the temperature sensor 252, if the temperature signal of the skin tissue is detected by the temperature sensor 252, it indicates that the electrode 24 corresponding to the temperature sensor 252 is in contact with the surface of the skin tissue. At this time, there is a current in the electrode 24 and the skin tissue is being treated.

When the detecting sensor is a current sensor 254, if a current signal is detected by the current sensor 254, it indicates that the electrode 24 corresponding to the current sensor 254 is in contact with the surface of skin tissue. At this time, there is a current in the electrode 24 and the skin tissue is being treated.

When the detecting sensor is a combination of the current sensor 254 and the voltage sensor 256, if the current sensor 254 detects a current signal and the corresponding voltage sensor 256 detects a voltage signal, the control unit 25 can calculate the resistance between the electrodes 24 according to the current signal and the voltage signal. According to the resistance, the control unit 25 can determine whether there is a current in the electrode 24 corresponding to the combination of the current sensor 254 and the voltage sensor 256, that is, whether the electrode 24 is in contact with the surface of skin tissue.

If there is a current in an electrode 24, it indicates that the skin tissue is being treated by this electrode 24. If there is no current in an electrode 24, it indicates that the skin tissue is not being treated by this electrode 24 and this electrode 24 is in an unused state. The use of the electrodes may be the state of each electrode 24 on the treatment head 23 in different periods of time. For example, for the first period and the second period that do not overlap each other, the use of the electrodes may be some electrodes 24 in use in the first period and some electrodes 24 in use in the second period.

S03, according to the usage of all electrodes 24 in the treatment head 23, determining the grouping mode of all electrodes 24 in the treatment head 23.

All electrodes 24 in use in a certain period of time are divided into the same set of electrodes.

It is known from the above description that all electrodes 24 in the treatment head 23 can be divided into multiple sets of electrodes according to any grouping mode. When the therapeutic apparatus 20 is in operation, at least one set of the multiple sets of electrodes is connected with the signal generator 21 through the switching circuit 22 to output the therapeutic signal. The following is described in detail in combination with the accompanying drawings and different embodiments: when the grouping mode is determined, how to select at least one set of electrodes to be connected with the signal generator 21 and output the therapeutic signal.

In some embodiments of the present application, the therapeutic apparatus 20 also includes a temperature sensor 252 arranged in the area where one set of electrodes among the multiple sets of electrodes are arranged. Referring to FIG. 27, in the embodiment of the present application, the step S100 of the above control method specifically includes:

S112, detecting a first temperature signal through the temperature sensor 252.

S114, according to the first temperature signal, choosing at least one set of electrodes from the multiple sets of electrodes.

The temperature signal here can be a changing temperature signal or a temperature signal with a temperature higher than a certain threshold.

Further, referring to FIG. 28, after step S200, it also includes:

S312, in the process of outputting the therapeutic signal by at least one set of electrodes, detecting a second temperature signal by the temperature sensor 252.

S314, according to the second temperature signal, adjusting a power and a frequency of the therapeutic signal outputted by the at least one set of electrodes.

In the embodiment of the present application, the frequency of the output therapeutic signal includes the time for continuously outputting the therapeutic signal in one cycle. For example, while the at least one set of electrodes output a therapeutic signal to the skin tissue, if the temperature signal detected by the temperature sensor 252 continues to rise, it indicates that the at least one set of electrodes is continuously outputting a therapeutic signal to the same position on the surface of the skin tissue. At this time, the control unit 25 can reduce the power and frequency of the at least one set of electrodes outputting the therapeutic signal, so as to avoid scalding the skin tissue. If the temperature signal detected by the temperature sensor 252 fluctuates continuously within a certain range, it indicates that the at least one set of electrodes is likely to move continuously on the surface of skin tissue. At this time, the power and frequency of the at least one set of electrodes outputting the therapeutic signal can be increased by the control unit 25, so as to improve the treatment effect. In the embodiment of the present application, the control unit 25 can adjust the power and frequency of the therapeutic signal output by the at least one group of electrodes, either by adjusting the output power and frequency of the signal generator 21, or by adjusting the opening and closing of the switching device 222 and the resistance of the voltage modulator 224.

In other embodiments of the present application, referring to FIG. 22, the therapeutic apparatus 20 also includes a current sensor 254. Referring to FIG. 29, in the embodiment of the present application, step S100 may also include:

S122, controlling the switch circuit 22 between the multiple sets of electrodes and the signal generator 21 to be turned on, making the multiple sets of electrodes connected with the signal generator 21 to output the therapeutic signal.

S124, in the process of outputting the therapeutic signal by the multiple sets of electrodes, detecting a first current signal by the current sensor 254.

S126, according to the first current signal, choosing at least one set of electrodes from the multiple sets of electrodes.

According to whether one set of electrodes among multiple sets of electrodes forms a current signal or not, it can be determined whether this set of electrodes is in contact with the surface of skin tissue.

Further, refer to FIG. 30, after step S200, it also includes:

S322, in the process of outputting the therapeutic signal by at least one set of electrodes, detecting a second current signal by the current sensor 254.

S324, according to the second current signal, adjusting a power and a frequency of the therapeutic signal outputted by the at least one set of electrodes.

For example, while the at least one set of electrodes output a therapeutic signal to the skin tissue, if the current signal detected by the current sensor 254 remains unchanged, it indicates that the at least one set of electrodes continuously outputs a therapeutic signal to the same position on the surface of the skin tissue. At this time, the power and frequency of the at least one group of electrodes outputting the therapeutic signal can be reduced by the control unit 25, so as to avoid scalding the skin tissue. If the current signal detected by the current sensor 254 is in a continuously changing state, it indicates that the at least one set of electrodes is likely to move continuously on the surface of skin tissue. At this time, the power and frequency of the at least one set of electrodes outputting the therapeutic signal can be increased by the control unit 25, so as to improve the treatment effect. Meanwhile, in the embodiment of the present application, the moving speed of the at least one set of electrodes on the surface of skin tissue can also be determined according to the change speed of the current signal. If the change speed of the current signal is fast, the moving speed of the at least one set of electrodes on the surface of the skin tissue is fast. At this time, the power and frequency of the at least one set of electrodes outputting the therapeutic signal can be appropriately increased. Conversely, if the change speed of the current signal is slow, the moving speed of the at least one set of electrodes on the surface of the skin tissue is slow. At this time, the power and frequency of the at least one set of electrodes outputting the therapeutic signal can be appropriately reduced. Similarly, in the embodiment of the present application, the control unit 25 can adjust the power and frequency of the therapeutic signal output by the at least one set of electrodes, either by adjusting the output power and frequency of the signal generator 21, or by adjusting the opening and closing of the switching device 222 and the resistance of the voltage regulator 224.

In other embodiments of the present application, referring to FIG. 23, the therapeutic apparatus 20 also includes a current sensor 254 and a voltage sensor 256. Referring to FIG. 31, in the embodiment of the present application, step S100 may also include:

S132, controlling the switch circuit 22 between the multiple sets of electrodes and the signal generator 21 to be turned on, making the multiple sets of electrodes connected with the signal generator 21 to output the therapeutic signal.

S134, in the process of outputting the therapeutic signal by the multiple sets of electrodes, detecting a first voltage signal by the voltage sensor 256.

S136, according to the first current signal and the first voltage signal, choosing at least one set of electrodes from the multiple sets of electrodes.

In the embodiment of the present application, the control unit 25 calculates the resistance value according to the current signal and voltage signal, and detects whether the electrode assembly is in contact with the skin tissue surface according to the resistance value, which can improve the accuracy of detecting whether the electrode assembly is in contact with the skin tissue surface.

Further, refer to FIG. 32, after step S200, it also includes:

S332, in the process of outputting the therapeutic signal by at least one set of electrodes, detecting a second voltage signal by the current sensor.

S334, according to the second current signal and the second voltage signal, adjusting a power and a frequency of the therapeutic signal outputted by the at least one set of electrodes.

For example, while the at least one set of electrodes outputs a therapeutic signal to the skin tissue, the current sensor 254 detects the current signal and the voltage sensor 256 detects the voltage signal. After acquiring the current signal and the voltage signal, the control unit 25 can obtain the resistance value between the electrodes 24 according to the current signal and the voltage signal. If the resistance value remains unchanged, it indicates that the at least one set of electrodes continuously output a therapeutic signal to the same position on the surface of the skin tissue. At this time, the control unit 25 can reduce the power and frequency of the at least one set of electrodes outputting the therapeutic signal, so as to avoid scalding the skin tissue. If the resistance value is continuously changing, it indicates that the at least one set of electrodes are constantly moving on the surface of skin tissue. At this time, the control unit 25 can increase the power and frequency of the at least one set of electrodes outputting the therapeutic signal, so as to improve the treatment effect. Meanwhile, in the embodiment of the present application, the moving speed of the at least one set of electrodes on the surface of skin tissue can also be determined according to the speed change of resistance value. If the speed of the resistance value changes fast, the moving speed of the at least one set of electrodes on the surface of the skin tissue is fast. At this time, the power and frequency of the at least one set of electrodes outputting the therapeutic signal can be appropriately increased. Conversely, if the speed of the resistance value changes slow, the moving speed of the at least one set of electrodes on the surface of the skin tissue is slow. At this time, the power and frequency of the at least one set of electrodes outputting the therapeutic signal can be appropriately reduced. Similarly, in the embodiment of the present application, the control unit 25 can adjust the power and frequency of the therapeutic signal output by the at least one set of electrodes, either by adjusting the output power and frequency of the signal generator 21, or by adjusting the opening and closing of the switching device 222 and the resistance of the voltage regulator 224.

It should be noted that the above current or resistance change data characterize the relative movement of the therapeutic apparatus on the surface of skin tissue, so we can use this as a speed sensor.

In other embodiments of the application, the therapeutic apparatus 20 also includes another speed sensor, such as a gyroscope. The speed sensor can be arranged in the therapeutic apparatus to detect the speed signal configured to characterize the moving speed of the therapeutic apparatus.

Referring to FIG. 33, after step S200, it also includes:

S342, in the process of outputting the therapeutic signal by at least one set of electrodes, detecting a speed signal by the speed sensor.

S344, according to the speed signal, adjusting a power and a frequency of the therapeutic signal outputted by the at least one set of electrodes.

In the embodiment of the present application, the speed signal can be detected directly through the speed sensor arranged in the therapeutic apparatus 20. When the speed signal indicates that the moving speed of the therapeutic apparatus is slow, the power and frequency of the at least one set of electrodes outputting the therapeutic signal can be appropriately reduced. When the speed signal indicates that the moving speed of the therapeutic apparatus is fast, the power and frequency of the at least one set of electrodes outputting the therapeutic signal can be appropriately increased.

In other embodiments of the present application, step S100 may also include: if the second control instruction is received, selecting at least one set of electrodes from multiple sets of electrodes according to the electrode selection mode indicated by the second control instruction.

The second control instruction here can be triggered by the user through a click operation, a sliding operation, a voice operation, a gesture operation, a somatosensory operation, etc. The second control instruction is used to indicate the electrode that the user wants to use and to specify at least one set of electrodes in the multiple sets of electrodes to communicate with the signal generator 21 through the switching circuit 22 and output the therapeutic signal.

Figure 34:
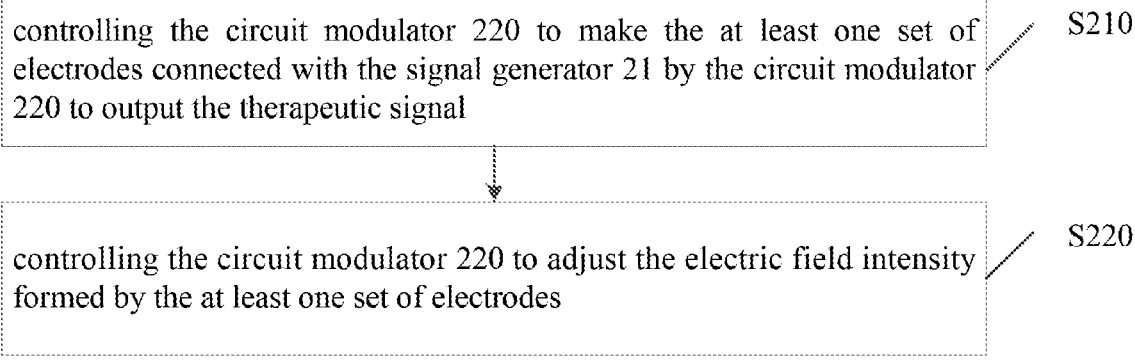
FIG. 34 is a flow chart of an output process of the electrode provided by the embodiment of the present application.

In the embodiment of the present application, referring to FIG. 18, the switching circuit 22 includes a circuit modulator 220. Referring to FIG. 34, in the embodiment of the present application, step S200 may include:

S210, controlling the circuit modulator 220 to make the at least one set of electrodes connected with the signal generator 21 by the circuit modulator 220 to output the therapeutic signal.

S220, controlling the circuit modulator 220 to adjust the electric field intensity formed by the at least one set of electrodes.

The circuit modulator 220 may include a switching device 222 and a voltage modulator 224 in series. The switching device 222 and the voltage modulator 224 are connected between the signal generator 21 and multiple sets of electrodes. The switching device 222 is used to control the on-off of the circuit between the signal generator 21 and multiple sets of electrodes. The voltage modulator 224 is used to control the electric field intensity formed by the electrode 24. In the embodiment of the present application, the switching circuit 22 between the at least one set of electrodes and the signal generator 21 can be turned on by controlling the closing of the switching device 222 between the at least one set of electrodes and the signal generator 21, so as to connect the at least one set of electrodes with the signal generator 21 and output the therapeutic signal. After that, the electric field intensity formed by the at least one set of electrodes outputting the therapeutic signal can also be controlled by controlling the voltage modulator 224.

It should be understood that the above different embodiments of the present application can be combined with each other to form a new embodiment. This can be obtained by those skilled in the art without paying creative labor according to the embodiment provided in the application. Therefore, the new technical solution formed by the combination of the above different embodiments of the application should also be understood to be within the protection scope of the application.

The embodiment of the application also provides a computer device. The computer device including a control unit, a memory, and a computer program stored in the memory and operable on the control unit is the above therapeutic apparatus. When the control unit executes the computer program, it realizes the steps of the control method in the therapeutic apparatus in the above embodiment.

The embodiment of the application also provides a computer-readable storage medium, which stores a computer program. When the computer program is executed by the control unit, the steps in the above method embodiments can be realized.

The embodiment of the present application provides a computer program product that makes the therapeutic apparatus to perform the steps in the above method embodiments when it is running on the therapeutic apparatus.

Those skilled in the art can realize that the units and algorithm steps of each example described in connection with the embodiments disclosed herein can be implemented in electronic hardware, or a combination of computer software and electronic hardware. Whether these functions are performed in hardware or software depends on the specific application and design constraints of the technical scheme. Professional technicians may use different methods to realize the described functions for each specific application, but such implementation should not be considered to be beyond the scope of the present application.

The invention claimed is:

1. A therapeutic apparatus comprising a signal generator configured for generating a therapeutic signal, a treatment head, multiple sets of electrodes arranged on the treatment head, a switch circuit connected between the signal generator and the multiple sets of electrodes, and a control unit connected with the switch circuit, and by the control unit controlling on-off of the switch circuit, the signal generator is controlled to be connected with at least one set of electrodes among the multiple sets of electrodes to output the therapeutic signal; the multiple sets of electrodes comprise working electrodes and regulating electrodes, and the regulating electrodes are configured for adjusting size and direction of an electric field formed by the working electrodes.

2. The therapeutic apparatus according to claim 1, wherein, the switch circuit comprises a circuit modulator connected between the signal generator and the multiple sets of electrodes, and the circuit modulator is connected with the control unit configured for controlling opening and closing of the circuit modulator and modulating a voltage of the connected electrodes through the circuit modulator.

3. The therapeutic apparatus according to claim 1, wherein, the multiple sets of electrodes are arranged on different areas of the treatment head.

4. The therapeutic apparatus according to claim 1, wherein, the therapeutic apparatus further comprises multiple temperature sensors connected with the control unit, and each temperature sensor is arranged in an area where electrodes are arranged.

5. The therapeutic apparatus according to claim 1, wherein, the therapeutic apparatus further comprises multiple current sensors connected with the control unit, and each current sensor is connected in series with one set of electrodes among the multiple sets of electrodes.

6. The therapeutic apparatus according to claim 1, wherein, the therapeutic apparatus further comprises multiple voltage sensors connected with the control unit, and each voltage sensor is connected in parallel with one set of electrodes among the multiple sets of electrodes.

7. The therapeutic apparatus according to claim 1, wherein, the therapeutic apparatus further comprises a speed sensor connected with the control unit.

8. The therapeutic apparatus according to claim 1, wherein, the therapeutic apparatus further comprises a detecting sensor connected with the control unit, and the detecting sensor is configured for detecting whether each of the multiple sets of electrodes is in working state.

9. A control method for controlling a control unit of a therapeutic apparatus which further comprises a signal generator configured for generating a therapeutic signal, a treatment head, multiple sets of electrodes arranged on the treatment head, a switch circuit connected between the signal generator and multiple sets of electrodes, wherein, the control method comprises:

step S1, choosing at least one set of electrodes from the multiple sets of electrodes;

step S2, controlling the switch circuit connected between the at least one set of electrodes and the signal generator to be turned on to connect the at least one set of electrodes and the signal generator to output a therapeutic signal;

before step S1 the control method further comprises:

step S0, if a first control instruction is detected, dividing all electrodes of the therapeutic apparatus into multiple sets of electrodes according to a grouping mode indicated by the first control instruction.

10. The control method according to claim 9, wherein, the therapeutic apparatus further comprises a detecting sensor connected with the control unit and configured for detecting whether each of the multiple sets of electrodes is in working state;

the control method further comprises:

controlling the switch circuit connected between all the electrodes in the treatment head and the signal generator to be turned on, making all the electrodes in the treatment head connected with the signal generator to output the therapeutic signal;

detecting sensing signals by the detecting sensor and determining usage of all electrodes in the treatment head according to the detected sensing signals;

according to the usage of all electrodes in the treatment head, determining the grouping mode of all electrodes in the treatment head.

11. The control method according to claim 9, wherein, the multiple sets of electrodes are arranged on different areas of the treatment head.

12. The control method according to claim 9, wherein, the therapeutic apparatus further comprises a temperature sensor connected with the control unit and arranged in an area where one set of electrodes among the multiple sets of electrodes are arranged;

the step S1 comprises:

detecting a first temperature signal through the temperature sensor;

according to the first temperature signal, choosing at least one set of electrodes from the multiple sets of electrodes;

after the step S2, the control method further comprises:

in the process of outputting the therapeutic signal by at least one set of electrodes, detecting a second temperature signal by the temperature sensor;

according to the second temperature signal, adjusting a power and a frequency of the therapeutic signal outputted by the at least one set of electrodes.

13. The control method according to claim 9, wherein, the therapeutic apparatus further comprises a current sensor connected with the control unit and connected in series with one set of electrodes among the multiple sets of electrodes;

the step S1 comprises:

controlling the switch circuit between the multiple sets of electrodes and the signal generator to be turned on, making the multiple sets of electrodes connected with the signal generator to output the therapeutic signal;

in the process of outputting the therapeutic signal by the multiple sets of electrodes, detecting a first current signal by the current sensor;

according to the first current signal, choosing at least one set of electrodes from the multiple sets of electrodes;

after the step S2, the control method further comprises:

in the process of outputting the therapeutic signal by at least one set of electrodes, detecting a second current signal by the current sensor;

according to the second current signal, adjusting a power and a frequency of the therapeutic signal outputted by the at least one set of electrodes.

14. The control method according to claim 13, wherein, the therapeutic apparatus further comprises a voltage sensor connected with the control unit and connected in parallel with one set of electrodes among the multiple sets of electrodes;

the step S1 comprises:

controlling the switch circuit between the multiple sets of electrodes and the signal generator to be turned on, making the multiple sets of electrodes connected with the signal generator to output the therapeutic signal;

in the process of outputting the therapeutic signal by the multiple sets of electrodes, detecting a first voltage signal by the voltage sensor;

according to the first current signal and the first voltage signal, choosing at least one set of electrodes from the multiple sets of electrodes;

after the step S2, the control method further comprises:

in the process of outputting the therapeutic signal by at least one set of electrodes, detecting a second voltage signal by the current sensor;

according to the second current signal and the second voltage signal, adjusting a power and a frequency of the therapeutic signal outputted by the at least one set of electrodes.

15. The control method according to claim 9, wherein, the therapeutic apparatus further comprises a speed sensor connected with the control unit, after the step S2, the control method further comprises:

in the process of outputting the therapeutic signal by at least one set of electrodes, detecting a speed signal by the speed sensor;

according to the speed signal, adjusting a power and a frequency of the therapeutic signal outputted by the at least one set of electrodes.

16. The control method according to claim 9, wherein, the switch circuit comprises a circuit modulator connected between the signal generator and the multiple sets of electrodes, and the circuit modulator is connected with the control unit configured for controlling opening and closing of the circuit modulator and modulating a voltage of the connected electrodes through the circuit modulator;

the step S2 comprises:

controlling the circuit modulator to make the at least one set of electrodes connected with the signal generator by the circuit modulator to output the therapeutic signal;

controlling the circuit modulator to adjust an electric field intensity formed by the at least one set of electrodes.

\* \* \* \* \*